US008846679B2

(12) United States Patent
Folger et al.

(10) Patent No.: US 8,846,679 B2
(45) Date of Patent: Sep. 30, 2014

(54) PHARMACEUTICAL COMPOSITION COMPRISING PIMOBENDAN

(75) Inventors: Martin A. Folger, Ingelheim (DE);
Bernhard Hassel, Ockenheim (DE);
Stefan Henke, Kirchen (DE); Jens Schmalz, Hueffelsheim (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 709 days.

(21) Appl. No.: 11/072,207

(22) Filed: Mar. 4, 2005

(65) Prior Publication Data
US 2005/0203097 A1 Sep. 15, 2005

(30) Foreign Application Priority Data

Mar. 8, 2004 (DE) .................. 10 2004 011 512

(51) Int. Cl.
| | | |
|---|---|---|
| *A61K 31/50* | (2006.01) | |
| *A61K 31/501* | (2006.01) | |
| *A61K 47/32* | (2006.01) | |
| *A61K 47/26* | (2006.01) | |
| *A61K 9/14* | (2006.01) | |
| *A61K 47/46* | (2006.01) | |
| *A61K 47/38* | (2006.01) | |
| *A61K 47/12* | (2006.01) | |

(52) U.S. Cl.
CPC .............. *A61K 47/46* (2013.01); *A61K 47/32* (2013.01); *A61K 47/26* (2013.01); *A61K 9/14* (2013.01); *A61K 31/501* (2013.01); *A61K 47/38* (2013.01); *A61K 47/12* (2013.01)
USPC ..................................... 514/252.06

(58) Field of Classification Search
None
See application file for complete search history.

(56) References Cited

U.S. PATENT DOCUMENTS

| | | | |
|---|---|---|---|
| 4,361,563 A | | 11/1982 | Austel et al. |
| 4,596,705 A | * | 6/1986 | Schepky et al. ............... 424/468 |
| 4,654,342 A | | 3/1987 | Slater |
| 4,868,182 A | | 9/1989 | Dage |
| 4,906,628 A | | 3/1990 | Coates |
| 4,954,501 A | | 9/1990 | Herter et al. |
| 5,024,998 A | | 6/1991 | Bodor |
| 5,151,420 A | | 9/1992 | Backstrom et al. |
| 5,364,646 A | | 11/1994 | Gruber et al. |
| 5,569,657 A | | 10/1996 | Nore et al. |
| 6,407,079 B1 | | 6/2002 | Muller et al. |

(Continued)

FOREIGN PATENT DOCUMENTS

| | | |
|---|---|---|
| CA | 2034569 A1 | 7/1991 |
| CA | 1336498 C | 8/1995 |

(Continued)

OTHER PUBLICATIONS

Merriam-Webster, homogeneous, Last Accessed Feb. 10, 2011, 2 pages, http://www.merriam-webster.com/dictionary/homogeneous.*

(Continued)

*Primary Examiner* — Trevor Love
(74) *Attorney, Agent, or Firm* — Michael P. Morris; Wendy M. Gombert

(57) ABSTRACT

The invention relates to novel solid formulations comprising as pharmaceutically active compound pimobendan and to processes for producing such solid formulations. The invention furthermore relates to a method for manufacturing a medicament for the prevention and/or treatment of congestive heart failure, wherein the solid formulations according to the invention are used.

24 Claims, 7 Drawing Sheets

(56) References Cited

U.S. PATENT DOCUMENTS

Figure 1:
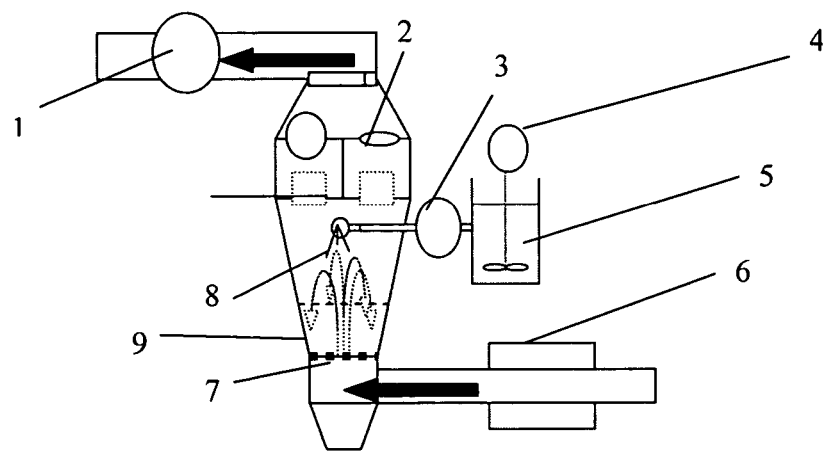

| | | | | |
|---|---|---|---|---|
| 6,476,078 | B1* | 11/2002 | Jerussi et al. | 514/646 |
| 2003/0162835 | A1* | 8/2003 | Staniforth et al. | 514/561 |
| 2003/0190343 | A1 | 10/2003 | Thombre et al. | |
| 2003/0212114 | A1 | 11/2003 | Sato | |
| 2004/0037869 | A1* | 2/2004 | Cleverly et al. | 424/442 |
| 2004/0157887 | A1 | 8/2004 | Whittle et al. | |
| 2005/0095293 | A1 | 5/2005 | Brauns et al. | |
| 2005/0203097 | A1 | 9/2005 | Folger et al. | |
| 2009/0082282 | A1 | 3/2009 | Daemmgen et al. | |
| 2011/0251208 | A1 | 10/2011 | Daemmgen et al. | |
| 2012/0148640 | A1 | 6/2012 | Folger et al. | |
| 2013/0203690 | A1 | 8/2013 | Daemmgen et al. | |

FOREIGN PATENT DOCUMENTS

| | | |
|---|---|---|
| CN | 1702243 A | 11/2005 |
| DE | 3728244 | 3/1989 |
| DE | 4001623 A1 | 7/1991 |
| EP | 0268146 A1 | 5/1988 |
| EP | 0306846 | 3/1989 |
| EP | 0330052 | 8/1989 |
| EP | 0335545 A2 | 10/1989 |
| EP | 439030 A2 | 7/1991 |
| EP | 1247456 A2 | 10/2002 |
| EP | 1260215 A1 | 11/2002 |
| EP | 1903039 A1 | 3/2008 |
| EP | 1920785 A1 | 5/2008 |
| GB | 2228004 A | 8/1990 |
| JP | H029825 A | 1/1990 |
| JP | H0570612 A | 3/1993 |
| JP | H11228302 A | 8/1999 |
| WO | 8502767 A1 | 7/1985 |
| WO | 0164190 A1 | 9/2001 |
| WO | 0197861 A2 | 12/2001 |
| WO | 0249646 A1 | 6/2002 |
| WO | 03012030 A2 | 2/2003 |
| WO | 03074032 A1 | 9/2003 |
| WO | 03097067 A1 | 11/2003 |
| WO | 03099194 A2 | 12/2003 |
| WO | 2004016252 A1 | 2/2004 |
| WO | 2004033444 A1 | 4/2004 |
| WO | 2004050657 A2 | 6/2004 |
| WO | 2004058726 A2 | 7/2004 |
| WO | 2005035505 A2 | 4/2005 |
| WO | 2005107756 A1 | 11/2005 |
| WO | 2006060122 A2 | 6/2006 |
| WO | 2006060127 A2 | 6/2006 |
| WO | 2010060874 A1 | 6/2010 |

OTHER PUBLICATIONS

Medline, homogeneous, Merriam-Webster, Last Accessed Feb. 10, 2011, 1 page, http://www.merriam-webster.com/medlineplus/homogeneous.*
Collins English Dictionary, homogeneous, Last Accessed Feb. 10, 2011, 1 page, http://www.xreferplus.com/entry/hcengdict/homogeneous.*
Chambers 21st Century Dictionary, homogeneous, Last Accessed Feb. 10, 2011, 1 page, http://www.xreferplus.com/entry/chambdict/homogeneous.*
Cambridge Dictionary, homogeneous, Last Accessed Feb. 10, 2011, 1 page, http://dictionary.cambridge.org/dictionary/british/homogeneous.*
The American Heritage Dictionary, homogeneous, Last Accessed Feb. 10, 2011, 1 page, http://www.xreferplus.com/entry/hmdictenglang/homogeneous.*
Pfizer, "Solid Oral Dosage Forms Powder Blending" and "Solid Oral Dosage Forms, Blend Uniformity: Principles and Examples", 2001, Pfizer, pp. 1-66.*
Bassani et al., "Enhanced Water-Solubility of Albendazole by Hydroxy-Propyl-β-Cyclodextrin Complexation". Journal of Inclusion Phenomena and Molecular Recognition in Chemistry, vol. 25, No. 1-3, Mar. 1996, pp. 149-152.
Borgarelli et al., "Canine Idiopathic Dilated Cardiomyopathy. Part II: Pathophysiology and therapy". The Veterinary Journal, vol. 162, 2001, pp. 182-195.
Calvert et al., "Congestive cardiomyopathy in Doberman Pinscher dogs". Journal of the American Veterinary Medical Association, vol. 181, 1982, pp. 598-602.
Calvert et al., "Signalment, Survival, and Prognostic Factors in Doberman Pinschers With End-Stage Cardiomyopathy". Journal of Veterinary Internal Medicine, vol. 11, No. 6, 1997, pp. 323-326.
Cowley et al, "Treatment of severe heart failure: quantity or quality of life? A trial of enoximone"., British Heart Journal, vol. 72, 1994, pp. 226-230.
Ettinger et al., "Effects of enalapril maleate on survival of dogs with naturally acquired heart failure". Journal of the American Veterinary Medical Association, vol. 213, No. 11, 1998, pp. 1573-1577.
Fitton et al., "Pimobendan. A Review of its Pharmacology and Therapeutic Potential in Congestive Heart Failure". Drugs and Aging, vol. 4, No. 5, 1994, pp. 417-441.
Fuentes, et al., "A Double-Blind, Randomized, Placebo-Controlled Study of Pimobendan in Dogs with Dilated Cardiomyopathy," Journal of Veterinary Internal Medicine, vol. 16, 2002, pp. 255-261.
Häggström et al., "New insights into degenerative mitral valve disease in dogs". Veterinary Clinics Small Animal Practice, vol. 34, 2004, pp. 1209-1226.
International Search Report and Written Opinion for PCT/EP2005/002133 mailed May 31, 2005.
Katz et al., "A multicenter, randomized, double-blind, placebo-controlled trial of pimobendan, a new cardiotonic and vasodilator agent, in patients with severe congestive heart failure". American Heart Journal, vol. 123, 1992, pp. 95-103.
Kubo et al, "Beneficial Effects of Pimobendan on Exercise Tolerance and Quality of Life in Patients with Heart Failure. Results of a Multicenter Trial". Circulation, vol. 85, No. 3, Mar. 1992, pp. 942-949.
Kvart et al., "Efficacy of Enalapril for Prevention of Congestive Heart Failure in Dogs with Myxomatous Valve Disease and Asymptomatic Mitral Regurgitation". Journal of Veterinary Internal Medicine, vol. 16, 2002, pp. 80-88.
Lai et al., "Real Time and Noninvasive Monitoring of Dry Powder Blend Homogeneity". AIChE Journal, vol. 47, No. 11, Nov. 2001, pp. 2618-2622.
McCrohon et al., "Differentiation of Heart Failure Related to Dilated Cardiomyopathy and Coronary Artery Disease Using Gadolinium-Enhanced Cardiovascular Magnetic Resonance". Circulation, vol. 108, Jul. 2003, pp. 54-59. Originally published online Jun. 23, 2003, http://circ.ahajournals.org, 7 pages.
Monnet et al., "Idiopathic Dilated Cardiomyopathy in Dogs: Survival and Prognostic Indicators". 1995, Journal of Veterinary Internal Medicine, vol. 9, No. 1, pp. 12-17.
O'Grady, et al., "Does Angiotensin Converting Enzyme Inhibitor Therapy Delay the Onset of Congestive Heart Failure or Sudden Death in Doberman Pinschers with Occult Dilated Cardiomyopathy?" Acvim Abstracts, 1997, p. 138.
Packer et al., "Effect of Oral Milrinone on Mortality in Severe Chronic Heart Failure." The New England Journal of Medicine, vol. 325, No. 21, Nov. 1991, pp. 1468-1475.
Piel et al., "Development of a parenteral and of an oral formulation of albendazole with cyclodextrins". S.T.P. Pharma Sciences, vol. 9, No. 3, 1999, pp. 257-260.
Remme et al., "Hemodynamic, Neurohumoral, and Myocardial Energetic Effects of Pimobendan, a Novel Calcium-Sensitizing Compound, in Patients with Mild to Moderate Heart Failure". Journal of Cardiovascular Pharmacology, vol. 24, No. 5, 1994, pp. 730-739.
Sisson, David, "Lecture Notes: Cardiology", The District of Columbia Academy of Veterinary Medicine, May 2001, pp. 1-18.
Conlon, P.D., "Nonsteroidal Drugs Used in the Treatment of Inflammation". Veterinary Clinics of North America: Small Animal Practice, vol. 18, No. 6, Nove. 1988, pp. 1115-1131.
Erhardt, L., "An Emerging Role for Calcium Sensitisation in the Treatment of Heart Failure". Expert Opinion on Investigational Drugs, vol. 14, No. 6, 2005, pp. 659-670.

(56) References Cited

OTHER PUBLICATIONS

Mamoru et al., "Effects of Long-term, Very-low-dose Pimobendan for Patients with Diastolic Heart Failure". Journal of Cardial Failure, vol. 12, No. 8, Oct. 2006, p. S171.
Ng, TZien M.H., "Levosimendan, a New Calcium-Sensitizing Inotrope for Heart Failure". Pharmacotherapy, vol. 24, No. 10, 2004, pp. 1366-1384.
Remme et al., "Hemodynamic Effects of Intravenous Pimobendan in Patients with Left Ventricular Dysfunction". Journal of Cardiovascular Pharmacology, vol. 15, Supp. 2, 1989, pp. S41-S44.
Rodriguez, Damon B., "Treatment of Feline Hypertrophic Cardiomyopathy*". Compendium, vol. 24, No. 6, Jun. 2002, pp. 470-476.
Van Meel et al., "Pimobendan Increases Survival of Cardiomyopathic Hamsters". Journal of Cardiovascular Pharmacology, vol. 13, 1989, pp. 508-509.
Sabbah et al., "Effects of long-term monotherapy with enalapril, metoprolol, and digoxin on the progression of left ventricular dysfuntion and dilation in dogs with reduced ejection fraction". Circulation, vol. 89, 1994, pp. 2852-2859.
Häggström et al., "Effects of long-term treatment with enalapril or hydralazine on the renin-angiotension-aldosterone system and fluid balance in dogs with naturally acquired mitral valve regurgitation". American Journal of Veterinary Research, vol. 57, No. 11, Nov. 1996, pp. 1645-1662.
Roland et al., "The Use of Pimobendan in Feline Heart Failure Secondary to Spontaneous Heart Disease". The 18th Annual ECVIM Congress, Abstract, Belgium, Sep. 2008, 1 page.
Fujino et al., "Differential Effects of d- and l-Pimobendan on Cardia Myofilament Calcium Sensitivity". The Journal of Pharmacology and Experimental Therapeutics, vol. 247, No. 2, 1988, pp. 519-523.
"Cardiovascular system". MIMS, IVS Annual, Chapter 5, 2003, p. 104.
"Citric Acid". The Merck Index, An Encyclopedia of Chemicals, Drugs, and Biologicals, 13th Edition, Merck Research Laboratories Division of Merck & Co., Inc., Whitehouse Station, NJ, Index 2350, 2001, pp. 405-406.
"Pharmaceutical Necessities". Remington's Pharmaceutical Sciences, 18th Edition, Mack Publishing Company, Easton, Pennsylvania, Chapter 66, 1990, pp. 1288-1300.
"Pimobendan". The Merck Index, An Encyclopedia of Chemicals, Drugs, and Biologicals, 13th Edition, Merck Research Laboratories Division of Merck & Co., Inc., Whitehouse Station, NJ, Index 7515, 2001, p. 1332.
Ahmed et al., "Pharmaceutical challenges in veterinary product development". Advanced Drug Delivery Reviews, vol. 54, 2002, pp. 871-882.
Asanoi et al., "Disparate Inotropic and Lusitropic Responses to Pimobendan in Conscious Dogs with Tachycardia-Induced Heart Failure". Journal of Cardiovascular Pharmacology, vol. 23, No. 2, 1994, pp. 268-274.
Atkins et al., "Guidelines for the Diagnosis and Treatment of Canine Chronic Valvular Heart Disease". Journal of Veterinary Internal Medicine, vol. 23, No. 6, 2009, pp. 1-9.
Boehringer Ingelheim Vetmedica GmbH, 1st International Canine Valvular Disease Symposium, Paris, Oct. 30-31, 2004, pp. 1-45.
Boehringer Ingelheim Vetmedica, Inc. "Freedom of Information Summary: Original New Animal Drug Application". NADA 141-273, Vetmedin, Pimobendan Chewable Tablets, Apr. 30, 2007, pp. 1-46.
Buchanan et al. "Vertebral scale system to measure canine heart size in radiographs". Journal of the American Veterinary Medical Association, vol. 206, No. 2, Jan. 1995, pp. 194-199.
Burlage et al., "Other Pharmaceutical Adjuncts"., Physical and Technical Pharmacy, The Blakiston Division: The McGraw-Hill Book Company, Inc., New York, 1963, pp. 653-662.
Gwathmey et al., "Abnormal Intracellular Calcium Handling in Myocardium From Patients With End-Stage Heart Failure". Circulation Research, vol. 61, No. 1, 1987, pp. 70-76.

Hauf et al., "Acute and Long-Term Hemodynamic Effects of Pimobendan (UD-CG 115 BS) in Comparison with Captopril". Journal of Cardiovascular Pharmacology, vol. 15, Supp. 2, 1989, pp. S49-S56.
Häggstrom et al., "Effect of Pimobendan or Benazepril Hydrochloride on Survival Times in Dogs with Congestive Heart Failure Caused by Naturally Occurring Myxomatous Mitral Valve Disease: The QUEST Study". Journal of Veterinary Internal Medicine, vol. 22, 2008, pp. 1124-1135.
Häggstrom et al., "Longitudinal Analysis of Quality of Life, Clinical, Radiographic, Echocardiographic, and Laboratory Variables in Dogs with Myxomatous Mitral Valve Disease Rexceiving Pimobendan or Benazepril: The QUEST Study". Journal of Veterinary Internal Medicine, 2013, pp. 1-11.
Iwasaki et al., "Pimobendan Inhibits the Production of Proinflammatory Cytokines and Gene Expression of Inducible Nitric Oxide Synthase in a Murine Model of Viral Myocarditis". Journal of the American College of Cardiology, vol. 33, No. 5, 1999, pp. 1400-1407.
Jain et al., "Effects of Milrinone on Left Ventricular Remodeling After Acute Myocardial Infarction". Circulation, vol. 84, No. 2, Aug. 1991, pp. 798-804.
Kashem et al., "CardioClasp: A New Passive Device to Reshape Cardiac Enlargement". ASAIO Journal, vol. 48, No. 3, 2002, pp. 253-259.
Kato, Kazuzo, "Clinical Efficacy and Safety of Pimobendan in Treatment of Heart Failure-Experience in Japan". Cardiology, vol. 88, Supp. 2, 1997, pp. 28-36.
Koob et al., "Acute Effects of Furosemide on Blood Electrolytes and Hemodynamics in Dogs". Angiology, 1978, pp. 463-472.
Lachman et al., "The Theory and Practice of Industrial Pharmacy"., 3rd Edition, Lea & Febiger, Philadelphia, 1986, pp. 58-60.
Lamb et al., "Assessment of the value of the vertebral heart scale in the radiographic diagnosis of cardia disease in dogs". Veterinary Record, vol. 146, 2000, pp. 687-690.
Liu et al., "Cardiovascular Pathology: The Role of Cardiovascular Pathology in Practice". Textbook of Canine and Feline Cardiology: Principles and Clinical Practice, Second Edition, Chapter 36, Saunders, 1999, pp. 817-844.
Lombard et al., "Clinical Efficacy of Pimobendan Versus Benazepril for the Treatment of Acquired Atrioventricular Valvular Disease in Dogs". Journal of the American Animal Hospital Association, vol. 42, No. 4, pp. 249-261, 2006.
Lord et al., "Radiology: Role of Radiology in Diagnosis and Management of Thoracic Disease". Textbook of Canine and Feline Cardiology: Principles and Clinical Practice, Second Edition, Chapter 7, Saunders, 1999, pp. 111-117.
Matsumori et al., "Pharmacology letters: Accelerated Communication: Pimobendan inhibits the activation of transcription factor NF-kB A mechanism which explains its inhibition of cytokine production and inducible nitric oxide synthase". Life Sciences, vol. 67, 2000, pp. 2513-2519.
Ohte et al., "The Cardia Effects of Pimobendan (But Not Amrinone) Are Preserved at Rest and During Exercise in Conscious Dogs with Pacing-Induced Heart Failure". The Journal of Pharmacology and Experimental Therapeutics, vol. 282, No. 1, 1997, pp. 23-31.
Pagel et al., "Influence of levosimendan, pimobendan, and milrinone on the regional distribution of cardiac output in anaesthetized dogs". British Journal of Pharmacology, vol. 119, 1996, pp. 609-615.
Permanetter et al., "Acute Effects of Intraveneous UD-CG 115 BS (Pimobendan) on the Cardiovascular System and Left Ventricular Pump Function". Journal of Cardiovascular Pharmacology, vol. 14, Supp. 2, 1989, pp. S36-S40.
Rackley, Charles E., "Diseases of the Heart and Pericardium"., The Merck Manual, Chapter 25, 16th Edition, 1992, pp. 446-459.
Rudnic et al., "Oral Solid Dosage Forms". Remington: The Science and Practice of Pharmacy, 20th Edition, Lippincott Williams & Wilkins, Baltimore, Maryland, Chapter 45, 2000, p. 858-870.
Saavedra et al., "Reverse Remodeling and Enhanced Adrenergic Reserve From Passive External Support in Experimental Dilated Heart Failure". Journal of the American College of Cariology, vol. 39, No. 12, 2002, pp. 2069-1076.

(56) References Cited

OTHER PUBLICATIONS

Sabbah, Hani N., "The Cardiac Support Device and the Myosplint: Treating Heart Failure by Targeting Left Ventricular Size and Shape". The Annals of Thoracic Surgery, vol. 75, 2003, pp. S13-S19.

Shiga et al., "b-Blocker Therapy Combined with Low-Dose Pimobendan in Patients with Idiopathic Dilated Cardiomyopathy and Chronic Obstructive Pulmonary Disease: Report on Two Cases". Cardiovascular Drugs and Therapy, vol. 16, 2002, pp. 259-263.

Sisson et al., "Myocardial Diseases of Dogs". Textbook of Canine and Feline Cardiology: Principles and Clinical Practice, Second Edition, Chapter 27, Saunders, 1999, pp. 581-619.

Summerfield et al., "Efficacy of Pimobendan in the Prevention of Congestive Heart Failure or Sudden Death in Doberman Pinschers with Preclinical Dilated Cardiomyopathy (The PROTECT Study)". Journal of Veterinary Internal Medicine, vol. 26, 2012, pp. 1337-1349.

Takeda et al., "Normalization of Left Ventricular Parameters Following Combined Pimobendan and Carvedilol Treatment in a Case of Unclassified Cardiomyopathy with Longstanding Refractory Status". Internal Medicine, vol. 41, No. 12, Dec. 2002, pp. 1147-1152.

Tomanek et al., "Growth of the Coronary Vasculature in Hypertrophy: Mechanisms and Model Dependence". Cellular and Molecular Biology Research, vol. 40, No. 2, 1994, pp. 129-136.

Wikipedia, the Free Encyclopedia, "Pimobendan". [Accessed at: http://en.wikipedia.org/wiki/Pimobenan on Mar. 10, 2014].

Dictionary of Veterinary Drugs and Animal Health Products Marketed in France, 12th Edition, 2003, 3 pages.

Lombard, Christophe W., "Therapy of Congestive Heart Failure in Dogs with Pimobendan". Proceedings of the 18th Annual Veterinary Medical Forum, American College of Veterinary Internatl Medicine, Seattle, WA, 2000, pp. 107-1093.

Luis-Fuentes, Virginia, "The effect of pimobendan in English Cocker Spaniels and Doberman dogs with heart failure and idiopathic dilated cardiomyopathy (DCM)". Ingelheimer Dialog, Boehringer Inglehim Vetmedica GmbH, Jun. 2000, Frankfort/Mainz, pp. 8-11.

Lewis, Alan B., "Clinical Profile and Outcome of Restrictive Cardiomyopathy in Children". American Heart Journal, vol. 123, No. 6, 1992, pp. 1589-1593.

Rinsyo to Kenkyu, "A case of diastolic hypertrophic cardiomyopathy in which sinus bradycardia and associated cardiac failure were improved as a result of cilostazol administration." The Japanese Journal of Clinical and Experimental Medicine, vol. 83, No. 5, May 2006, pp. 125-130.

Loftsson et al., "Pharmaceutical Applications of Cyclodextrins. 1. Drug Solubilization and Stabilization". Journal of Pharmaceutical Sciences, vol. 85, No. 10, Oct. 1996, pp. 1017-1025.

Abstract in English of JPH0570612, 1993.

Kittleson et al., "The Acute Hemodynamic Effects of Milrinone in Dogs With Severe Idiopathic Myocardial Failure". Journal of Veterinary Medicine, vol. 1, 1987, pp. 121-127.

Abstract in English of JPH11228302, 1999.

Abstract in English for CN1702243A, 2005.

Goineau et al., "Cardiomyopathic Syrian Hamster as a Model of Congestive Heart Failure". Current Protocols in Pharmacology, Supp. 42, Unit 5.50, John Wiley & Sons, Inc., Sep. 2008, 12 pages.

Bastien et al., "Chronic AT receptor blockade and angiotensin-converting enzyme (ACE) inhibition in (CHF 146) cardiomyopathic hamsters: effects on cardiac hypertrophy and survival". Cardiovascular Research, vol. 43, 1999, pp. 77-85.

Côté et al., "Congestive Heart Failure". Feline Cardiology, Ch. 19, Wiley-Blackwell, ISBN 978-0-8138-1242-7, 2011, p. 259.

Fox et al., "Prosepective Double-Blinded, Multicenter Evaluation of Chronic Therapies for Feline Diastolic Heart Failure: Interim Analysis". ACVIM Abstracts, Abstract 78, 2003, pp. 398-399.

Fox, Philip R., "Hypertrophic Cardiomyopathy. Clinical and Pathologic Correlates". Journal of Veterinary Cardiology, vol. 5, No. 2, Nov. 2003, pp. 39-45.

Baur et al., "Cardiac remodelling and myocardial contractility in patients with congestive heart failure treated with furosemide and enalapril". Basic Research in Cardiology, vol. 86, Supp. 1, 1991, pp. 157-163.

Hasenfuss et al., "Influence of the calcium-sensitizer UDCG-115 on hemodynamics and myocardial energetics in patients with idiopathic dilated cardiomyopathy. Comparison with nitroprusside". Basic Research Cardiology, vol. 84, No. 1, 1989, pp. 225-233.

Kato et al., "Clinical Evaluation of Pimobendan (UD-CG115BS) for Chronic Heart Failure—A Multicentre Placebo-Controlled Double Blind Study". Journal of Clinical Therapeutics & Medicines, vol. 8, No. 6, 1992, pp. 1311-1351.

Wikipedia, the Free Encyclopedia, "Milrinone". [Accessed at: http://en.wikipedia.org/wiki/Milrinone on Mar. 10, 2014].

Vidal et al., "Making sense of antisense". European Journal of Cancer, vol. 41, 2005, pp. 2812-2818.

Pirollo et al., "Targeted Delivery of Small Interfering RNA: Approaching Effective Cancer Therapies". Cancer Research, vol. 68, No. 5, Mar. 2008, pp. 1247-1250.

Phillips et al., "The challenge of gene therapy and DNA delivery". Journal of Pharmacy and Pharmacology, vol. 53, 2001, pp. 1169-1174.

\* cited by examiner

PHARMACEUTICAL COMPOSITION COMPRISING PIMOBENDAN

1. BACKGROUND OF THE INVENTION

1. Technical Field

The invention relates to the field of animal health. In particular, the invention relates to novel oral pharmaceutical compositions comprising, as part of the pharmaceutically active compounds, pimobendan.

2. Background Information

Pimobendan, (4,5-dihydro-6-[2-(4-methoxyphenyl)-1H-benzimidazol-5-yl]-5-methyl-3(2H)-pyridazone) is disclosed in U.S. Pat. No. 4,361,563, herein incorporated by reference in its entirety. Pimobendan is a cardiotonic, hypotensive and anti-thrombotic. Said substance is useful in the treatment of congestive heart failure.

Pimobendan hardly dissolves in water. The resorption of pimobendan when administered orally is prone to considerable inter- and intra-individual fluctuations if the active substance is incorporated in known or conventional pharmaceutical forms for oral administration. The reason for this is that pimobendan is characterized by a low solubility in aqueous media and a very highly pH-dependent solubility. To overcome this, hard gelatine capsules were used containing pimobendan formulated with citric acid, in particular at a weight ratio of pimobendan to citric acid of between 1:10 and 1:20 (U.S. Pat. No. 5,364,646, herein incorporated by reference in its entirety). However, the high quantity of citric acid and the acidic taste of citric acid is not readily accepted by most animals—thus, such capsules have to be force-fed to the animals or mixed with food prior to application.

The problem underlying the present invention was to provide a pimobendan solid formulation readily acceptable by mammalian subjects, especially small animals.

2. BRIEF SUMMARY OF THE INVENTION

The invention relates to novel solid formulations comprising as a pharmaceutically active compound pimobendan or a pharmaceutically acceptable salt thereof which is homogenously dispersed in a polyvalent acid and a flavor acceptable to small animals. Preferably, such solid formulations are granules or tablets. Most preferred is a tablet characterized in that the tablet comprises, 1.25 mg, 2.5 mg, 5 mg or 10 mg pimobendan, and further comprises lactose, corn starch, croscarmellose-sodium, citric acid, preferably at an amount of 50 mg/g of the solid formulation, artificial beef flavor, polyvidone, colloidal anhydrous silica and magnesium stearate.

The invention further relates to fluid-bed granulation processes for production of the solid formulations comprising the following steps:

a) an aqueous solution of pimobendan and a binder as defined above is sprayed onto a solid carrier bed comprising one or more carriers and/or excipients, flavor and citric acid anhydride and
b) the resulting mixture is dried and
c) the dried mixture is sieved and de-agglomerated and
d) a flow regulator is added to the sieved and de-agglomerated mixture and
e) a lubricant is added to the resulting mixture and
f) the resulting mixture with lubricant is blended for uniformity of granules to obtain final granules and/or
g) the final granules are compressed to solid formulations. Step g) is omitted if the solid formulation is a granule. If the solid formulation is a tablet, step g) is carried out.

Furthermore, the invention relates to a method of prevention and/or treatment of diseases wherein cardiotonic, hypotensive and anti-thrombotic substances have a therapeutic benefit, comprising administering to a mammal in need of such treatment a therapeutically effective amount of a solid formulation prepared as described above.

Preferred is a method of prevention and/or treatment of congestive heart failure, comprising administering to a mammal in need of such treatment a therapeutically effective amount of a solid formulation according to the invention as disclosed above. Most preferably, the method comprises administering a tablet according to the invention, as defined above.

Furthermore, the invention relates to a method for manufacturing a medicament for the prevention and/or treatment of congestive heart failure, Additionally, the invention relates to a method for manufacturing a medicament for the prevention and/or treatment of congestive heart failure, characterised in that a tablet comprising, 1.25 mg, 2.5 mg, 5 mg or 10 mg pimobendan and further comprising lactose, corn starch, croscarmellose-sodium, 50 mg/g citric acid, artificial beef flavor, polyvidone, colloidal anhydrous silica and magnesium stearate is made.

3. BRIEF DESCRIPTION OF THE DRAWINGS

Figure 2:
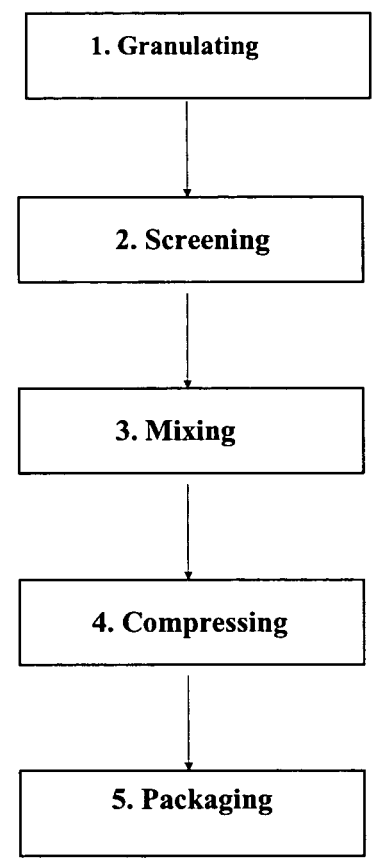

FIG. 1: Illustration of the basic top spray fluid bed process Reference signs: 1 Exhaust air ventilator; 2 Filter; 3 Pump; 4 Stirrer; 5 Aqueous Suspension of micronised pimobendan and binder solution (PVP, HPMC, starch, gelatine); 6 Heating device for inlet air; 7 Sieve; 8 Nozzle, aqueous suspension is sprayed onto powder bed (citric acid, lactose, starch, flavour); 9 Powder bed FIG. 2: Flow Chart of Manufacturing Process FIG. 3: Dissolution Profiles, Pimobendan 1.25 mg tablets, showing 95% confidence intervals of the mean; USP apparatus 2 (Paddle), Rotation Speed 75 rpm, Buffer pH 4.0. Comparison of dissolution profiles of tablets which were stored 1 and 6 months at 40° C./75% in HDPE bottles; batch no. PB020049

Figure 4:
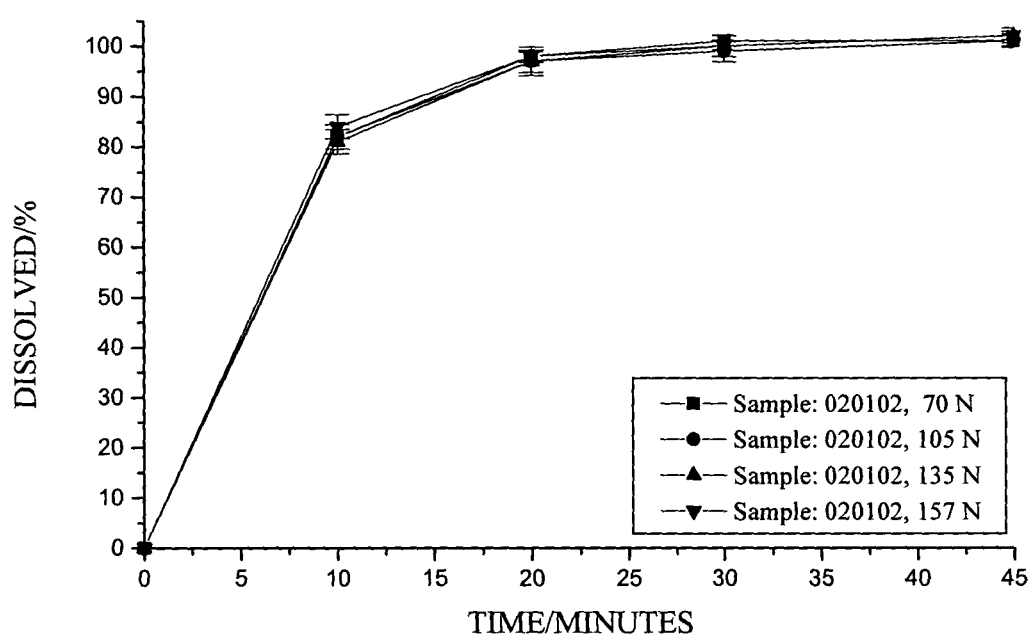

FIG. 4: Dissolution Profiles, Pimobendan 1.25 mg tablets, showing 95% confidence intervals of the mean; USP apparatus 2 (Paddle), Rotation Speed 75 rpm, Buffer pH 4.0. Comparison of dissolution profiles of tablets which were stored 12 days at 25° C./60% in open glass bottles; batch no. PB010080

Figure 5:
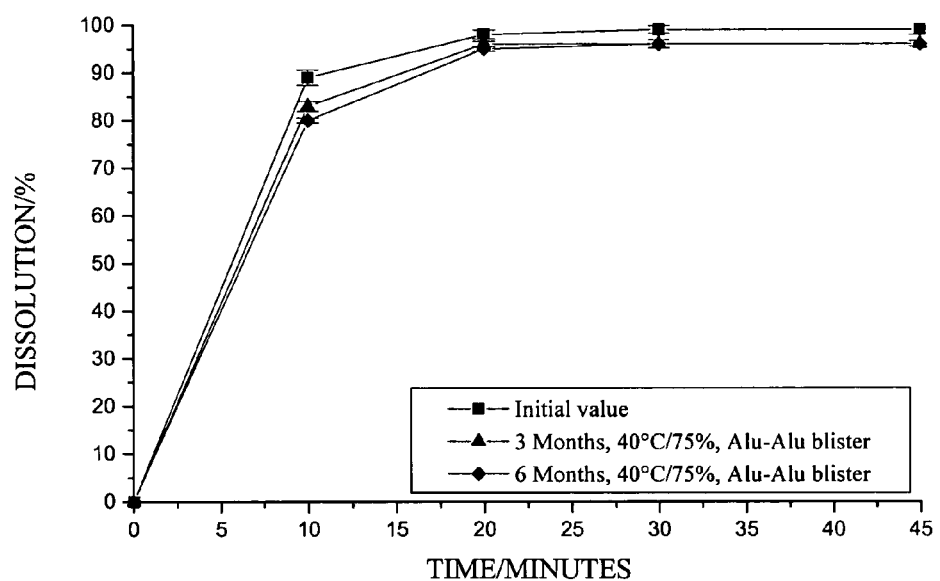

FIG. 5: Dissolution Profiles, Pimobendan 2.5 mg tablets, showing 95% confidence intervals of the mean; USP apparatus 2 (Paddle), Rotation Speed 75 rpm, Buffer pH 4.0. Comparison of dissolution profiles of tablets which were stored 3 and 6 months at 40° C./75% in Alu-Alu Blister; batch no. PB010076

Figure 6:
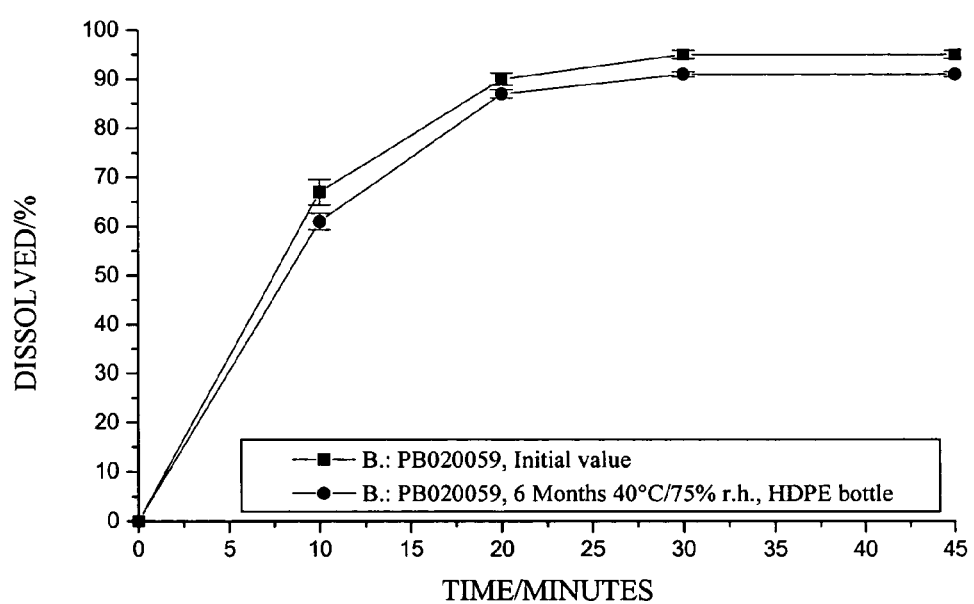

FIG. 6: Dissolution Profiles, Pimobendan 5.0 mg tablets, showing 95% confidence intervals of the mean; USP apparatus 2 (Paddle), Rotation Speed 75 rpm, Buffer pH 4.0. Comparison of dissolution profiles of tablets which were stored 6 months at 40° C./75% in HDPE bottles; batch no. PB020059

Figure 7:
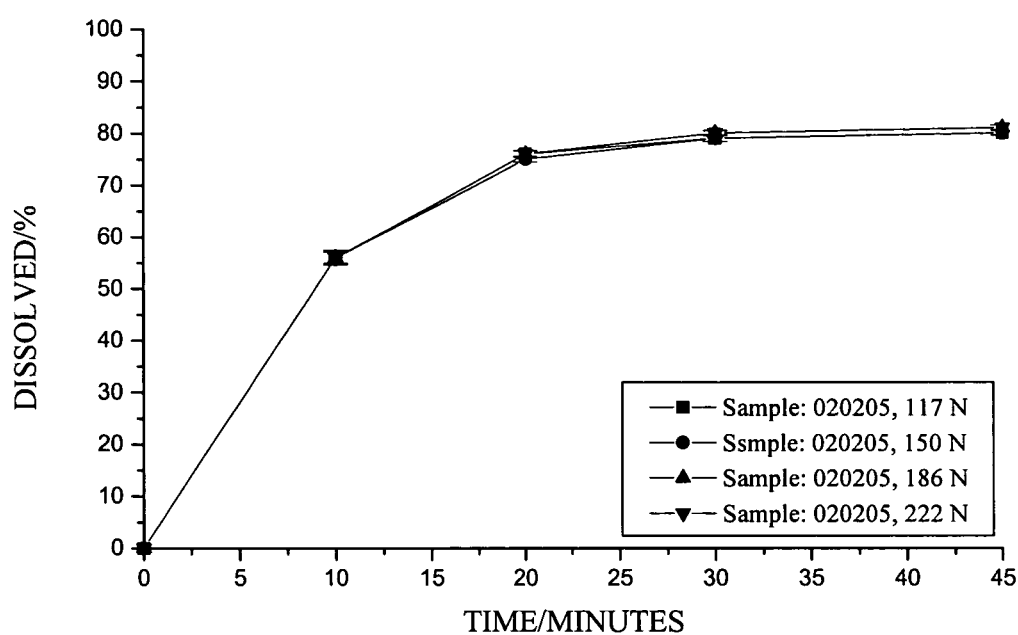

FIG. 7: Dissolution Profiles, Pimobendan 5.0 mg tablets, showing 95% confidence intervals of the mean; USP apparatus 2 (Paddle), Rotation Speed 75 rpm, Buffer pH 4.0. Manufacturing variable: Different compression forces; batch no. PB020205

4. DETAILED DESCRIPTION OF THE INVENTION

Before the embodiments of the present invention it must be noted that as used herein and in the appended claims, the singular forms "a", "an", and "the" include plural reference unless the context clearly dictates otherwise. Thus, for example, reference to "a tablet" includes a plurality of such tablets, reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art. Accordingly, the term "about" is not used in the description. Although any methods and materials similar or equivalent to those described herein can be used in the practice or testing of the present invention, the preferred methods, devices, and materials are described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The solution to the above technical problem is achieved by the description and the embodiments characterized in the claims.

To overcome the difficulties in the art, a process was invented. Only the invention of this novel, fluid-bed granulation process allowed the formulation of solid formulations according to the invention. With the process according to the invention, it was possible to formulate a long-term stable, capable of being produced on a large scale, homogenously dispersed, fast-releasing solid formulation. Despite the large size, pimobendan was homogenously dispersed. Such solid formulations comprise a flavor suitable for small animals, which surprisingly still allows a formulation having a polyvalent acid and yet have a palatability rate of more than 70%—in many cases more than 90%. Thus, the solid formulations according to the invention are a major step forward in therapeutic application as they do not have to be force-fed to the animal.

In a first important embodiment, the invention relates to a solid formulation, comprising pimobendan or a pharmaceutically acceptable salt thereof, see e.g. U.S. Pat. No. 4,361,563 or U.S. Pat. No. 5,364,646 (both herein incorporated by reference in its entirety), which is homogenously dispersed in a polyvalent acid selected from the group consisting of citric acid, acetic acid, maleic acid, tartaric acid and the anhydride of any of said polyvalent acids and mixtures thereof, and a flavor acceptable to small animals. Such flavors according to the invention preferably are selected from artificial beef flavours, artificical chicken flavours, pork liver extract, artificial meat flavour, honey flavour and the like. Said flavors not only disguise the taste of the polyvalent acid, but also the taste of pimobendan.

Preferably, the solid formulation according to the invention is a tablet or granule formulation. The granule formulation according to the invention is explained in more detail below. More preferably, the solid formulation is chewable.

The invention preferably also relates to a solid formulation according to the invention, further comprising one or several pharmaceutically acceptable excipients. Excipients according to the invention are preferably selected from the group consisting of diluents, disintegrants, carriers, binders, flow regulators, lubricants and solvents. Any other excipients known to the skilled person and found suitable for the solid formulation according to the invention may also be comprised in the solid formulation according to the invention. See also Remington, J. P. The science and Practice of Pharmacy (2000). 20th ed. Lippincott Williams & Wilkins Publishers, Philiadelphia, US. More preferably, said excipients are carriers/disintegrants selected from the group lactose, starch, cellulose, microcrystalline cellulose and cellulose derivatives, e.g. methylcellulose, and the like. Any other carrier known to the skilled person and found suitable for the solid formulation according to the invention may also form part of the solid formulation according to the invention. See also Remington, J. P. The science and Practice of Pharmacy (2000). 20th ed. Lippincoft Williams & Wilkins Publishers, Philiadelphia, US.

One or several binders according to the invention are preferably selected from the group consisting of polyvidone (used synonymously for povidone), methylcellulose, hydroxypropylmethylcellulose (HPMC), hydroxymethylcellulose, starch, gelatine, and the like. Any other binder known to the skilled person and found suitable for the solid formulation according to the invention may also be comprised in the solid formulation according to the invention. See also Remington, J. P. The science and Practice of Pharmacy (loc. cit.).

The solid formulation according to the invention may also comprise one or several flow regulators selected from the group consisting of silica, preferably colloidal anhydrous silica, calcium silicate, magnesium silicate, talc, and the like. Any other flow regulator known to the skilled person and found suitable for the solid formulation according to the invention may also be incorporated into the solid formulation according to the invention. See also Remington, J. P. The science and Practice of Pharmacy (loc. cit.).

The solid formulation according to the invention may also comprise one or several disintegrants selected from the group consisting of croscarmellose sodium, sodium starch glycolate, pregelatinised starch, cross-linked polyvinylpyrrolidone and the like. Any other disintegrant known to the skilled person and found suitable for the solid formulation according to the invention may also form part of the solid formulation according to the invention. See also Remington, J. P. The science and Practice of Pharmacy (loc. cit.).

The solid formulation according to the invention may also comprise one or several lubricants selected from the group consisting of magnesium stearate, calcium stearate, glyceryl behenate, polyethylene glycol, stearic acid, talc and the like. Any other lubricant known to the skilled person and found suitable for the solid formulation according to the invention may form part of the solid formulation according to the invention. See also Remington, J. P. The science and Practice of Pharmacy (loc. cit.).

The invention preferably also relates to a solid formulation according to the invention, characterized in that the carriers are starch and lactose. The invention preferably also relates to a solid formulation according to the invention, characterized in that the lactose consists of coarse particles greater than 200 μm in size. The person skilled in the art knows other types of lactose which are suitable as well as carrier according to the invention, e.g. fine lactose equal or smaller than 200 μm in size or spray-dried lactose. Preferred is lactose consisting of coarse particles greater than 200 μm in size.

The invention preferably also relates to a solid formulation according to the invention, characterized in that the starch or various starches are selected from the group consisting of native starch, gelatinized starch, partly gelatinized starch, starch powder, starch granules, chemically modified starch and swellable, physically modified starch.

The invention preferably also relates to a solid formulation according to the invention, characterized in that the starch is corn starch.

The invention preferably also relates to a solid formulation according to the invention, comprising 0.5 to 20 mg of pimobendan. The more preferred solid formulation contains 1 to 10 mg of pimobendan. The even more preferred solid formulation contains 1.25 to 5 mg of pimobendan. Most preferred solid formulations contain 1.25 mg, 2.5 mg, 5 mg or 10 mg of pimobendan.

The invention preferably also relates to a solid formulation according to the invention, comprising a content of 1:10-1:40 of pimobendan in relation to citric acid anhydride. The preferred ratio is 1:20.

The invention preferably also relates to a solid formulation according to the invention, characterized in that the weight of the whole solid formulation is in the range of 250 to 3000 mg, with a more preferred weight range of 500 mg to 2000 mg, and most preferred weight of 500 mg, 1000 mg or 2000 mg.

The invention preferably also relates to a solid formulation according to the invention, characterized in that the solid formulation is produced by a fluid-bed granulation process comprising or consisting of the steps:
  a) an aqueous solution of pimobendan and a binder as defined above is sprayed onto a solid carrier bed comprising one or several carriers and/or excipients as defined above, flavor and citric acid anhydride and
  b) the mixture of a) is dried and
  c) the mixture of b) is sieved and de-agglomerated and
  d) a flow regulator is added to the mixture of c) and
  e) a lubricant is added to the mixture of d) and
  f) the mixture of e) is blended for uniformity of granules to obtain final granules and/or
  g) the final granules of f) are compressed to solid formulations.

Step g) is omitted if the solid formulation is a granule. If the solid formulation is a tablet, step g) is carried out.

The invention preferably also relates to a solid formulation according to the invention, characterized in that the solid formulation is produced by a fluid-bed granulation process comprising or consisting of the steps:
  a) an aqueous solution of pimobendan and povidone is sprayed onto a solid carrier bed comprising lactose, starch, flavor and citric acid anhydride and
  b) the mixture of a) is dried and
  c) the mixture of b) is sieved and de-agglomerated and
  d) a flow regulator is added to the mixture of c) and
  e) a lubricant is added to the mixture of d) and
  f) the mixture of e) is blended for uniformity of granules to obtain final granules and/or
  g) the final granules of f) are compressed to solid formulations.

Step g) is omitted if the solid formulation is a granule. If the solid formulation is a tablet, step g) is carried out.

The invention preferably relates to a granule formulation as obtained by the process above that can either be administered in the granular form or as tablets after compressing the final granules to tablets. Therefore, the solid formulation according to the invention preferably is a granule (or a plurality of such granules) or a tablet. The administration of the granules can take place by mixing with food or by offering the granules directly to the animal, e.g. in a bowl. The application of the granular form will allow an individual dosing of pimobendan according to the body weight of the animal.

The tablets according to the invention have surprising advantages. The dissolution profile ensures immediate release of pimobendan. Surprisingly, it could be demonstrated that while compressing the final granules as mentioned above, a decrease in the dissolution characteristics is not observed. By ensuring an immediate release profile of pimobendan, the amount of drug to be administered can be kept as low as possible, thereby improving the safety profile, which is especially important for long-term treatment.

Furthermore, the dosing accuracy of the tablet is excellent. This is due to the fact that in accordance with the manufacturing process according to this invention, an excellent uniformity of pimobendan content is achieved. Furthermore, the tablets can be broken into two halves so that half the dose per tablet can be administered. Compared with the existing gelatine capsule, the dosing accuracy and compliance of both the animal and the animal owner are assured. This is even more important since the drug is administered for a chronic condition and long-term treatment.

Also, the palatability of the tablet is excellent. More than 90% of the dogs to whom the tablet according to this invention was given accepted the tablet voluntarily with only the tablet offered in a bowl. Compared with the existing gelatine capsule, the ease of administration has increased compliance with the prescribed treatment regime. This is important since the drug is administered for a chronic condition.

The invention preferably also relates to a tablet according to the invention, characterized in that the tablet is stable for at least 18 months at 25° C. and 60% relative humidity. In the examples, testing parameter assays are disclosed for degradation of pimobendan, dissolution, loss on drying, hardness and disintegration of the tablet. The tablets according to the invention are within the specification limits regarding degradation of pimobendan, dissolution, loss on drying, hardness and disintegration.

Suitable packaging materials for tablets according to the invention are selected from, but not limited to: aluminum/aluminum blisters, PVC/PVDC blisters, and HDPE (high density polyethylene bottles).

The invention preferably also relates to a tablet according to the invention, characterized in that the tablet is oblong in shape. For such a tablet, characteristics like crushing strength, disintegration, uniformity of weight and content uniformity fulfill the requirements of the European Pharmacopoeia (ISBN/ISSN 92-871-5106-7 of $4^{th}$ Edition 2004, Vol. 4.8, European Directorate for the Quality of Medicines (EDQM), European Pharmacopoeia, 226 avenue de Colmar, F-67029 Strasbourg, France, http://www.pheur.org) and the United States Pharmacopoeia (http://www.usp.org; in print: USP-NF, catalog No. 2270001).

The invention preferably relates to a solid formulation, and most preferred a tablet according to the invention, characterized in that the solid formulation or tablet comprising 0.5-20 mg pimobendan, preferably of 1.25 mg, 2.5 mg, 5 mg or 10 mg pimobendan, and further comprises lactose (35-50% by weight relative to the dry mass of the solid formulation/tablet=(w/w)), corn starch (25-50% w/w), croscarmellose-sodium (1-5%), citric acid (2.5-10% w/w), artificial beef flavor (5-30% w/w), polyvidone (1-5% w/w), colloidal anhydrous silica (0.1-1, preferably 0.1-0.5% w/w) and magnesium stearate (0.25-1.5% w/w), wherein the percentage by weight of pimobendan contains preferably about 0.25% (w/w) and the sum of the percentages by weight of all ingredients of the solid formulation including pimobendan is 100% (w/w). A skilled man is in a position to prepare such solid formulations, preferably a tablet. Thus, the skilled man knows that he can add to 0.25% (w/w) pimobendan at most 32,625% (w/w) corn starch, 4% (w/w) croscarmellose-sodium 5% (w/w) citric acid, 20% (w/w) artificial beef flavor, 4% (w/w) polyvidone, colloidal, 0.5% (w/w) anhydrous silica, 1% (w/w) magnesium stearate if the amount of lactose to be 32,625% (w/w). Moreover, the skilled man also knows, that if he decided to reduce the amount of the artificial beef flavor, for example, to the minimum of 5% (w/w), he can increase the amount of lactose, for example, to 47,625% (w/w). The invention also relates to a solid formulation, preferably a tablet, comprising about 0.25% (w/w) pimobendan and any of the above other ingredients of the solid formulation, preferably the tablet, in the range given above so that the sum of the amounts by weight of the individual formulation ingredients is 100%.

The present invention is also directed to a solid formulation, preferably to a tablet, which comprises 1 mg pimobendan, 100-200 mg lactose, 100-200 mg corn starch, 4-20 mg croscarmellose-sodium, 10-40 mg citric acid anhydrous, 20-120 mg artificial beef flavor, 4-20 mg polyvidone, 0.4-4 mg colloidal anhydrous silica, and 1-6 mg magnesium stearate for each 400 mg of total weight of the solid formulation, preferably a tablet. According to a further embodiment of the present invention, the solid formulation, preferably the tablet, comprises 1 mg pimobendan, 120-180 mg lactose, 120-180 mg corn starch, 8-18 mg croscarmellose-sodium, 15-30 mg citric acid anhydrous, 40-100 mg artificial beef flavor, 8-18 mg polyvidone, 0.5-2 mg colloidal anhydrous silica, and 2-5 mg magnesium stearate for each 400 mg of total weight of the solid formulation/tablet. For example, the present invention relates to a solid formulation comprising for each 400 mg of total weight: 1 mg pimobendan, 20 mg citric acid anhydrous, 130.5 mg lactose, 130.5 mg corn starch, 16 mg polyvidone, 16 mg croscarmellose-sodium, 80 mg artificial beef flavor, 4 mg magnesium stearate, and 2 mg colloidal anhydrous silica. A skilled man is in a position to prepare such solid formulation/tablet. The skilled man also knows that he can vary the amount of each ingredient of the solid formulation/tablet within the ranges given above in that the total weight of the solid formulation/tablet for each 1 mg pimobendan is 400 mg. For example, the amount of lactose may be 100, 101, 102, . . . 108, 109, 110 etc.; 111, 112, . . . 118, 119, 120 etc; 121, 122, . . . 128, 129, 120 etc; 131, 132, . . . 138, 139, 140 etc; 141, 142, . . . 148, 149, 150 etc; 151, 152, . . . 158, 159, 160 etc; 161, 162, . . . 168, 169, 170 etc; 171, 172, . . . 178, 179, 180 etc; 108, 182, . . . 188, 189, 190 etc; 191, 192, . . . 198, 199, 200 mg for each 400 mg of total weight of the solid formulation, preferably a tablet, comprising about 1 mg pimobendan. In the same manner the amount of corn starch may be 100, 101, 102, . . . 108, 109, 110 etc.; 111, 112, . . . 118, 119, 120 etc; 121, 122, . . . 128, 129, 120 etc; 131, 132, . . . 138, 139, 140 etc; 141, 142, . . . 148, 149, 150 etc; 151, 152, . . . 158, 159, 160 etc; 161, 162, . . . 168, 169, 170 etc; 171, 172, . . . 178, 179, 180 etc; 108, 182, . . . 188, 189, 190 etc; 191, 192, . . . 198, 199, 200 mg for each 400 mg of total weight of the solid formulation, preferably a tablet, comprising about 1 mg pimobendan. Furthermore, the amount of citric acid anhydrous may be 10, 11, 12, . . . 18, 19, 20 etc.; 21, 22, . . . 28, 29, 30 etc; 31, 32, . . . 38, 39, 40 mg for each 400 mg of total weight of the solid formulation, preferably a tablet comprising about 1 mg pimobendan. Furthermore, the amount of artificial beef flavor may be 20, 21, 22, 28, 29, 30 etc.; 31, 32, . . . 38, 39, 40 etc; 41, 42, . . . 48, 49, 50 etc; 50, 51, 52, 58, 59, 60 etc.; 61, 62, . . . 68, 69, 70 etc; 71, 72, . . . 78, 79, 80 etc, 81, 82, 83, . . . 88, 89, 90 etc.; 91, 92, . . . 98, 99, 100 etc; 101, 102, . . . 108, 109, 110 etc; 111, 112, . . . 118, 119, 120 mg for each 400 mg of total weight of the solid formulation, preferably a tablet, comprising about 1 mg pimobendan. Furthermore, the amount of polyvidone may be 4, 5, 6, . . . 8, 9, 10 etc.; 11, 12, . . . 18, 19, 20 mg for each 400 mg of total weight of the solid formulation, preferably a tablet, comprising about 1 mg pimobendan. Furthermore, the amount of croscarmellose-sodium may be 4, 5, 6, . . . 8, 9, 10 etc.; 11, 12, . . . 18, 19, 20 mg for each 400 mg of total weight of the solid formulation, preferably a tablet, comprising 1 mg pimobendan. Furthermore, the amount of magnesium stearate may be 1.0, 1.1, 1.2, . . . 1.8, 1.9, 2.0 etc.; 2.1, 2.2, . . . 2.8, 2.9, 3.0 etc; 3.1, 3.2, . . . 3.8, 3.9, 40 etc; 4.0, 4.1, 4.2, . . . 4.8, 4.9, 5.0 etc.; 5.1, 5.2, . . . 5.8, 5.9, 6.0 mg for each 400 mg of total weight of the solid formulation, preferably a tablet, comprising about 1 mg pimobendan. Furthermore, the amount of colloidal anhydrous silica may be 0.4, 0.5, 0.6, 0.7, 0.8, 0.9 1.0, 1.1, 1.2, . . . 1.8, 1.9, 2.0 etc.; 2.1, 2.2, . . . 2.8, 2.9, 3.0 etc; 3.1, 3.2, . . . 3.8, 3.9, 4.0 mg for each 400 mg of total weight of the solid formulation, preferably a tablet, comprising about 1 mg pimobendan. A skilled man is in a position to prepare any of such inventive solid formulation, preferably as a tablet.

In another important embodiment, the invention relates to a fluid-bed granulation process comprising the following steps:
a) an aqueous solution of pimobendan and a binder as defined above is sprayed onto a solid carrier bed comprising one or several carriers and/or excipients as defined above, flavor and citric acid anhydride and
b) the mixture of a) is dried and
c) the mixture of b) is sieved and de-agglomerated and
d) a flow regulator is added to the mixture of c) and
e) a lubricant is added to the mixture of d) and
f) the mixture of e) is blended for uniformity of granules to obtain final granules and/or
g) the final granules of f) are compressed to solid formulations.

Step g) is omitted if the solid formulation is a granule. If the solid formulation is a tablet, step g) is carried out.

The invention preferably relates to a fluid-bed granulation process comprising the following steps:
a) an aqueous solution of pimobendan and polyvidone is sprayed onto a solid support comprising lactose, starch, flavor and citric acid anhydride and
b) the mixture of a) is dried and
c) the mixture of b) is sieved and de-agglomerated and
d) a flow regulator is added to the mixture of c) and
e) a lubricant is added to the mixture of d) and
f) the mixture of e) is blended for uniformity of granules to obtain final granules and/or
g) the final granules of f) are tabletted.

Step g) is omitted if the solid formulation is a granule. If the solid formulation is a tablet, step g) is carried out.

Another embodiment is a method of prevention and/or treatment of diseases wherein cardiotonic, hypotensive and anti-thrombotic substances have a therapeutic benefit, comprising administering to a mammal in need of such treatment a therapeutically effective amount of a solid formulation according to the invention as disclosed above. Preferred is a method of prevention and/or treatment of congestive heart failure, comprising administering to a mammal in need of such treatment a therapeutically effective amount of a solid formulation according to the invention as disclosed above. Most preferably, the method comprises administering a tablet according to the invention, characterized in that the tablet comprises 1.25 mg, 2.5 mg, 5 mg or 10 mg pimobendan, and further comprises lactose, corn starch, croscarmellose-sodium, citric acid preferably at an amount of 50 mg/g, artificial beef flavor, polyvidone, colloidal anhydrous silica and magnesium stearate. Preferably also, such treatment is by orally administering the solid formulation according to the invention.

The mammal according to the invention is preferably a mammal selected from the group consisting of dogs, cats and rodents such as rabbits.

Furthermore, the invention relates to a method for manufacturing a medicament for the prevention and/or treatment of congestive heart failure, characterised in that a solid formulation according to the invention is used. Preferably, the invention relates to a method for manufacturing a medicament for the prevention and/or treatment of congestive heart failure, characterised in that a tablet consisting of 1.25 mg, 2.5 mg, 5 mg or 10 mg pimobendan and further consisting of lactose, corn starch, croscarmellose-sodium, 50 mg/g citric acid, artificial beef flavor, polyvidone, colloidal anhydrous silica and magnesium stearate is used.

The present invention furthermore relates to a kit, which comprises a solid formulation, preferably a tablet according to the present invention described herein, and a package leaflet or user instruction including the information concerning how the solid formulation, preferably the tablet, is to used via the oral route for the prevention and/or treatment of congestive heart failure in a mammal in need of such prevention or treatment, preferably in a dog, cat or rodent.

5. EXAMPLES

The following examples serve to further illustrate the present invention; but the same should not be construed as limiting the scope of the invention disclosed herein.

Example 1

Compositions

| | | Composition A | | | | |
|---|---|---|---|---|---|---|
| | Ingredients | mg/tablet 1.25 mg chewable | mg/tablet 2.5 mg chewable | mg/tablet 5.0 mg chewable | Volatile ingredient | kg/batch |
| (01) | Pimobendan | 1.250 | 2.500 | 5.000 | | 0.175 |
| (02) | Citric acid anhydrous <200 μm | 25.000 | 50.000 | 100.000 | | 3.500 |
| (03) | Starch | 163.125 | 326.250 | 652.500 | | 22.8375 |
| (04) | Lactose, coarse | 163.125 | 326.250 | 652.500 | | 22.8375 |
| (05) | Polyvidone | 20.000 | 40.000 | 80.000 | | 2.800 |
| (06) | Croscarmellose Sodium | 20.000 | 40.000 | 80.000 | | 2.800 |
| (07) | Artificial Powdered Beef Flavour | 100.000 | 200.000 | 400.000 | | 14.000 |
| (08) | Silica, colloidal anhydrous | 2.500 | 5.000 | 10.000 | | 0.350 |
| (09) | Magnesium stearate | 5.000 | 10.000 | 20.000 | | 0.700 |
| (10) | Purified water | | | | + | |
| | | 500.000 | 1000.000 | 2000.000 | — | 70.000 |

| | Composition B | | | | |
|---|---|---|---|---|---|
| Ingredients | mg/tablet 1.25 mg chewable | mg/tablet 2.5 mg chewable | mg/tablet 5.0 mg chewable | Volatile ingredient | kg/batch |
| Pimobendan | 1.250 | 2.500 | 5.000 | | 0.175 |
| Citric acid anhydrous <200 μm | 25.000 | 50.000 | 100.000 | | 3.500 |
| Starch | 163.125 | 326.250 | 652.500 | | 22.8375 |
| Lactose, coarse | 238.125 | 476.250 | 952.500 | | 22.8375 |
| Polyvidon | 20.000 | 40.000 | 80.000 | | 2.800 |
| Croscarmellose Sodium | 20.000 | 40.000 | 80.000 | | 2.800 |
| Meat Flavour | 25.000 | 50.000 | 100.000 | | 14.000 |
| Silica, colloidal anhydrous | 2.500 | 5.000 | 10.000 | | 0.350 |
| Magnesium stearate | 5.000 | 10.000 | 20.000 | | 0.700 |
| Purified water | | | | + | |
| | 500.000 | 1000.000 | 2000.000 | — | 70.000 |

Example 2

Raw Materials

| | | |
|---|---|---|
| (01) | Pimobendan | |
| | Function: | Active ingredient |
| (02) | Citric acid anhydrous <200 μm | |
| | Function: | Diluent, Disintegrant |
| (03) | Starch | |
| | Function: | Carrier, Disintegrant |
| (04) | Lactose coarse | |
| | Function: | Carrier, Disintegrant |
| (05) | Povidone | |
| | Function: | Binder |
| (06) | Croscarmellose Sodium | |
| | Function: | Disintegrant |
| (07) | Artificial Powdered Beef Flavour | |
| | Function: | Flavour |
| (08) | Silica, colloidal anhydrous | |
| | Function: | Flow regulator, Disintegrant |
| (09) | Magnesium stearate | |
| | Function: | Lubricant |
| (10) | Purified water | |
| | Function: | Solvent |

Example 3

Product Description

Appearance: Brownish, Oblong Tablets, with Breakline.

| | Tablet | Tablet | Tablet |
|---|---|---|---|
| Weight | 500 mg | 1000 mg | 2000 mg |
| Length | About 19.0 mm | About 24.0 mm | About 25.0 mm |
| Width | About 7.0 mm | About 7.5 mm | About 15.0 mm |
| Thickness | About 4.2 mm | About 5.6 mm | About 6.0 mm |

Example 4

Manufacturing Process 1 batch=140000 tablets (1.25 mg Dosage)
1 batch=70000 tablets (2.50 mg Dosage)
1 batch=35000 tablets (5.00 mg Dosage)

| | |
|---|---|
| 1. Granulating | |
| Transfer in a suitable Granulator after prescreening: | |
| (01) Starch (e.g. 18 mesh sieve) | 22.8375 kg |
| (02) Lactose (e.g. 18 mesh sieve) | 22.8375 kg |
| (03) Citric acid (e.g. 18 mesh sieve) | 3.500 kg |
| (04) Croscarmellose sodium (e.g. 18 mesh sieve) | 2.800 kg |
| (05) Artificial Beef Flavour (e.g. 45 mesh sieve) | 14.000 kg |
| (05) Povidone (Spray solution) | 2.800 kg |
| (06) UDCG 115 BS (Spray liquid) | 0.175 kg |
| Premix in the granulator and granulate | |
| | 68.950 kg |
| Purified water (e.g. 16.8 kg, range: 12.0–18.0 kg) is used as a solvent for the spray solution of povidone and dispersion of pimobendan. | |
| 2. Screening | |
| Screen the premixture 1. | 68.950 kg |
| | 68.950 kg |
| 3. Final mixing | |
| Add | |
| (07) Silica, colloidal anhydrous (e.g. 25 mesh sieve) | 0.350 kg |
| (08) Magnesium stearate (e.g. 25 mesh sieve) | 0.700 kg |
| In a tumbling mixer, mix the screened premixture (2.) and the two ingredients | 70.000 kg |
| | 70.000 kg |
| 4. Compression | |
| Using a rotary press, compress the final mixture (3.) into tablets of 500 mg, 1000 mg, 2000 mg. | 70.000 kg |
| | 70.000 kg |
| 5. Packaging | |
| Transfer the tablets in a suitable container. The tablets can be packed e.g. by blistering of the tablets in a suitable machine. | |

Example 5

In Process Controls

| | | |
|---|---|---|
| 1. Granules | | |
| 1.1 Appearance: | Brownish, white-speckled granules | |
| 1.2 Loss on Drying: | Determine the loss on drying e.g.: HR73; 3 g/105° C./5 min Target: approx. 3.0% Tolerance limits: below 5.0% | |
| 2. Tablets | | |
| 2.1 Appearance: | Brownish, white-speckled, oblong tablets with breakline | |
| 2.2 Weight uniformity: | | |
| | 1) 1.25 mg chewable | Average weight: 475–525 mg |
| | 2) 2.5 mg chewable | Average weight: 950–1050 mg |
| | 3) 5 mg chewable | Average weight: 1900–2100 mg |
| 2.3 Hardness: | Determine the hardness | |
| | 1) 1.25 mg | Target: 140 N Tolerance: 60–250 N |
| | 2) 2.5 mg | Target: 160 N Tolerance: 60–250 N |
| | 3) 5.0 mg | Target 190 N Tolerance: 60–300 N |
| 2.4 Disintegration time: | Determine the disintegration time according to USP/EP Tolerance limits: ≤15 minutes with water at 37° C., with disks | |

Example 6

Palatability Study

A study to investigate the palatability of pimobendan-containing tablets was carried out. For a period of four days, two products were given to twenty or ten dogs, respectively, for voluntary uptake. For example, the following formulations with a content of 5 mg/500 mg active ingredient were examined:

| Ch. 010122 (tablets with 10% content of artificial beef flavor) | | Ch. 010123 (tablets with 10% content of artificial beef flavor) | |
|---|---|---|---|
| Pimobendan (UD-CG 115 BS) | 5 mg | Pimobendan (UD-CG 115 BS) | 5 mg |
| Lactose | 85.5 mg | Lactose | 55.5 mg |
| Corn starch | 199.5 mg | Corn starch | 129.5 mg |
| Croscarmellose-Sodium | 20 mg | Croscarmellose-Sodium | 20 mg |

-continued

| | Ch. 010122 (tablets with 10% content of artificial beef flavor) | | Ch. 010123 (tablets with 10% content of artificial beef flavor) | |
|---|---|---|---|---|
| Citric acid | 100 | mg | Citric acid | 100 mg |
| Artificial Beef Flavor | 50 | mg | Artificial Beef Flavor | 150 mg |
| Polyvidone | 25 | mg | Polyvidone | 25 mg |
| Macrogol 6000 | 15 | mg | Macrogol 6000 | 15 mg |
| | Total: 500 mg | | Total: 500 mg | |

In case of Ch. 010123 in competition with the identical formulation in granulated format, a voluntary uptake was observed in 36 out of 40 possible opportunities (i.e. when offered to 10 dogs for 10 days). This compares to an acceptance rate of 90.0%.

In case of Ch. 010222 in competition with a formulation in granulated format of equal quantity with 30% flavor, a voluntary uptake was observed in 31 out of 40 possible opportunities. This compares to an acceptance rate of 77.5%.

Example 7

Dissolution Profiles

Figure 3:
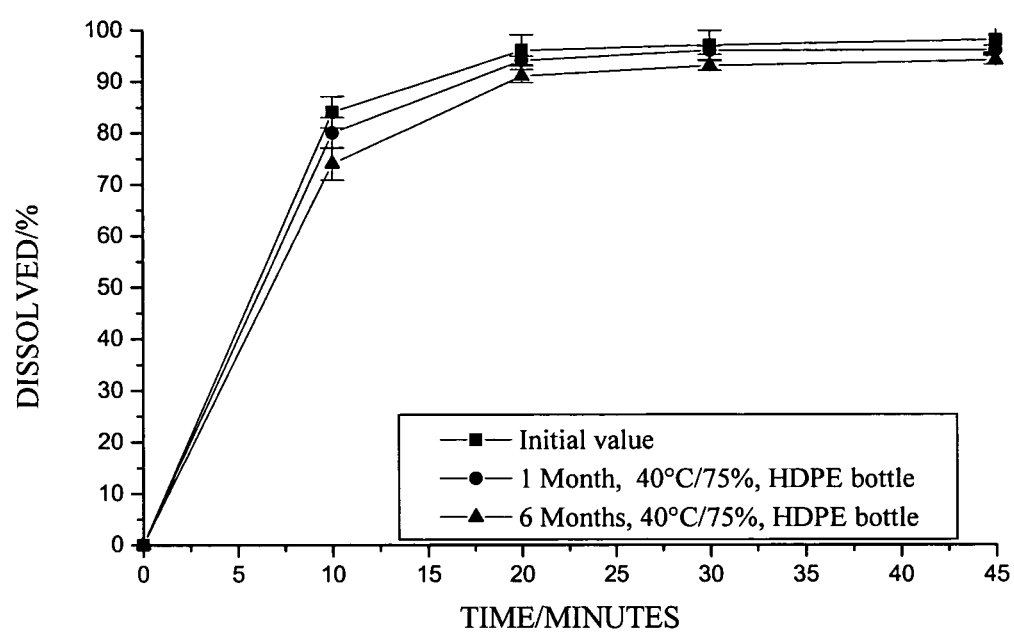

Examples for representative dissolution profiles of the tablet according to this invention are as disclosed in FIG. 3.
DISSOLUTION PROFILES, PIMOBENDAN 1.25 MG TABLETS SHOWING 95% CONFIDENCE INTERVALS OF THE MEAN
USP APPARATUS 2 (PADDLE), ROTATION SPEED 75 RPM, BUFFER pH 4.0 COMPARISON OF DISSOLUTION PROFILES OF TABLETS WHICH WERE STORED 1 AND 6 MONTHS AT 40° C./75% IN HDPE BOTTLES
BATCH NO. PB020049
Examples for representative dissolution profiles of the tablet according to this invention are as disclosed in FIG. 4.
DISSOLUTION PROFILES, PIMOBENDAN 1.25 MG TABLETS SHOWING 95% CONFIDENCE INTERVALS OF THE MEAN
USP APPARATUS 2 (PADDLE), ROTATION SPEED 75 RPM, BUFFER pH 4.0 COMPARISON OF DISSOLUTION PROFILES OF TABLETS WHICH WERE STORED 12 DAYS AT 25° C./60% IN OPEN GLASS BOTTLES
BATCH NO. PB010080
DISSOLUTION PROFILES, PIMOBENDAN 1.25 MG TABLETS
MANUFACTURING VARIABLE: DIFFERENT COMPRESSION FORCES

| | | % Dissolved, mean (n = 6) Tablet hardness | | | |
|---|---|---|---|---|---|
| Batch No. | Time (min) | 70 N | 105 N | 135 N | 157 N |
| 020102 | 10 | 82 | 82 | 81 | 84 |
| | 20 | 98 | 97 | 97 | 98 |
| | 30 | 101 | 99 | 100 | 100 |
| | 45 | 101 | 101 | 102 | 102 |

Examples for representative dissolution profiles of the tablet according to this invention are as disclosed in FIG. 5.
DISSOLUTION PROFILES, PIMOBENDAN 2.5 MG TABLETS SHOWING 95% CONFIDENCE INTERVALS OF THE MEAN
USP APPARATUS 2 (PADDLE), ROTATION SPEED 75 RPM, BUFFER pH 4.0 COMPARISON OF DISSOLUTION PROFILES OF TABLETS WHICH WERE STORED 3 AND 6 MONTHS AT 40° C./75% IN ALU-ALU BLISTER
BATCH NO. PB010076
Examples for representative dissolution profiles of the tablet according to this invention are as disclosed in FIG. 6.
DISSOLUTION PROFILES, PIMOBENDAN 5.0 MG TABLETS SHOWING 95% CONFIDENCE INTERVALS OF THE MEAN
USP APPARATUS 2 (PADDLE), ROTATION SPEED 75 RPM, BUFFER pH 4.0 COMPARISON OF DISSOLUTION PROFILES OF TABLETS WHICH WERE STORED 6 MONTHS AT 40° C./75% 1N HDPE BOTTLES
BATCH NO. PB020059
Examples for representative dissolution profiles of the tablet according to this invention are as disclosed in FIG. 7.
DISSOLUTION PROFILES, PIMOBENDAN 5.0 MG TABLETS SHOWING 95% CONFIDENCE INTERVALS OF THE MEAN
USP APPARATUS 2 (PADDLE), ROTATION SPEED 75 RPM, BUFFER pH 4.0 MANUFACTURING VARIABLE: DIFFERENT COMPRESSION FORCES
BATCH NO. 020205

| | | % Dissolved, mean (n = 6) Tablet hardness | | | |
|---|---|---|---|---|---|
| Batch No. | Time (min) | 117 N | 150 N | 186 N | 222 N |
| 020205 | 10 | 56 | 56 | 56 | 56 |
| | 20 | 76 | 75 | 76 | 76 |
| | 30 | 79 | 79 | 80 | 80 |
| | 45 | 80 | 80 | 81 | 81 |

Analytical Results for Pimobendan Chewable Tablet Batches Used in Stability Study

| Tablet strength | Batch No. | Packaging | % dissolved in t = 30 minutes, mean (n = 6) | | | |
|---|---|---|---|---|---|---|
| | | | Initial value | 6 Months 25° C./60% | 6 Months 30° C./70% | 6 Months 40° C./75% |
| 1.25 mg | PB020049 | HDPE bottle | 97 | 95 | 94 | 93 |
| | PB020049 | Alu—Alu blister | | 95 | 93 | 94 |
| | PB020049 | PVC/PVDC blister | | 94 | 93 | 93 |
| | PB020050 | HDPE bottle | 94 | 92 | 93 | 91 |
| | PB020050 | Alu—Alu blister | | 92 | 92 | 91 |
| | PB020050 | PVC/PVDC blister | | 93 | 93 | 92 |
| | PB020051 | HDPE bottle | 94 | 93 | 92 | 92 |
| | PB020051 | Alu—Alu blister | | 94 | 93 | 92 |
| | PB020051 | PVC/PVDC blister | | 93 | 93 | 91 |

-continued

| Tablet strength | Batch No. | Packaging | Initial value | % dissolved in t = 30 minutes, mean (n = 6) | | |
|---|---|---|---|---|---|---|
| | | | | 6 Months 25° C./60% | 6 Months 30° C./70% | 6 Months 40° C./75% |
| 2.5 mg | PB020052 | HDPE bottle | 98 | n.d. | n.d. | 93 |
| | PB020052 | Alu—Alu blister | | n.d. | n.d. | 94 |
| | PB020052 | PVC/PVDC blister | | n.d. | n.d. | 92 |
| | PB020053 | HDPE bottle | 97 | n.d. | n.d. | 91 |
| | PB020053 | Alu—Alu blister | | n.d. | n.d. | 91 |
| | PB020053 | PVC/PVDC blister | | n.d. | n.d. | 91 |
| | PB020054 | HDPE bottle | 97 | n.d. | n.d. | 91 |
| | PB020054 | Alu—Alu blister | | n.d. | n.d. | 92 |
| | PB020054 | PVC/PVDC blister | | n.d. | n.d. | 91 |
| 5.0 mg | PB020059 | HDPE bottle | 95 | 93 | 92 | 92 |
| | PB020059 | Alu—Alu blister | | 93 | 92 | 92 |
| | PB020059 | PVC/PVDC blister | | 92 | 92 | 91 |
| | PB020060 | HDPE bottle | 92 | 91 | 90 | 89 |
| | PB020060 | Alu—Alu blister | | 91 | 91 | 90 |
| | PB020060 | PVC/PVDC blister | | 91 | 91 | 89 |
| | PB020061 | HDPE bottle | 94 | 91 | 91 | 89 |
| | PB020061 | Alu—Alu blister | | 92 | 92 | 90 |
| | PB020061 | PVC/PVDC blister | | 91 | 91 | 89 | n.d. = not determined

Example 8

Content Uniformity

Samples were taken from both the final blend before tabletting and from the tabletting process. The following results demonstrate the uniformity of pimobendan content.

Blend Uniformity

| Batch | Assay[mg/g] | % Target |
|---|---|---|
| 0007LP - A | 2.37 | 94.8 |
| 0007LP - B | 2.48 | 99.2 |
| 0007LP - C | 2.43 | 97.2 |
| 0007LP - D | 2.44 | 97.6 |
| 0007LP - E | 2.47 | 98.8 |
| 0007LP - F | 2.50 | 100.0 |
| 0007LP - G | 2.49 | 99.6 |
| 0007LP - H | 2.49 | 99.6 |
| 0007LP - I | 2.50 | 100.0 |
| 0007LP - J | 2.43 | 97.2 |
| Average | 2.46 | 98.4 |
| 0008LP - A | 2.41 | 96.4 |
| 0008LP - B | 2.48 | 99.2 |
| 0008LP - C | 2.45 | 98.0 |
| 0008LP - D | 2.45 | 98.0 |
| 0008LP - E | 2.46 | 98.4 |
| 0008LP - F | 2.43 | 97.2 |
| 0008LP - G | 2.46 | 98.4 |
| 0008LP - H | 2.44 | 97.6 |
| 0008LP - I | 2.47 | 98.8 |
| 0008LP - J | 2.50 | 100.0 |
| Average | 2.46 | 98.2 |

Uniformity of Process

| Batch | Assay [mg/g] | % Target |
|---|---|---|
| PM020080 - 1 | 2.48 | 99.2 |
| PM020080 - 2 | 2.52 | 100.8 |
| PM020080 - 3 | 2.50 | 100.0 |
| PM020080 - 4 | 2.52 | 100.8 |
| PM020080 - 5 | 2.49 | 99.6 |
| PM020080 - 6 | 2.52 | 100.8 |
| Average | 2.51 | 100.2 |
| PM020081 - 1 | 2.45 | 98.0 |
| PM020081 - 2 | 2.51 | 100.4 |
| PM020081 - 3 | 2.48 | 99.2 |
| PM020081 - 4 | 2.45 | 98.0 |
| PM020081 - 5 | 2.47 | 98.8 |
| PM020081 - 6 | 2.45 | 98.0 |
| Average | 2.47 | 98.7 |

Example 9

Accuracy of Broken Tablets

The tablets according to this invention were part of an content uniformity test for the broken tablets. 10 tablets were taken from the beginning, middle and end of the tabletting process and broken into two halves. The pimobendan content was determined.

| Pimobendan 5 mg tablet, batch no. 0000251607 | | | | |
|---|---|---|---|---|
| | Specification | Start | Middle | End |
| CU min. (mg) | ≥2.13 | 2.44 | 2.43 | 2.41 |
| CU max. (mg) | ≤2.87 | 2.61 | 2.57 | 2.57 |
| CU average (mg | 2.25–2.62 | 2.52 | 2.51 | 2.50 |
| RSD (%) | ≤6.0 | 2.3 | 1.9 | 2.0 |

| Pimobendan 1.25 mg tablet, batch no. 0000251604 | | | | |
|---|---|---|---|---|
| | Specification | Start | Middle | End |
| CU min. (mg) | ≥0.532 | 0.577 | 0.590 | 0.582 |
| CU max. (mg) | ≤0.718 | 0.664 | 0.650 | 0.645 |
| CU average (mg | 0.563–0.656 | 0.621 | 0.621 | 0.616 |
| RSD (%) | ≤6.0 | 5.4 | 3.4 | 3.6 |

Example 10

Stability Data After 24 Months (Dissolution/Assay of Pimobendan/Degradation of Pimobendan)

| | | Product: Pimobendan chewable tablets 1.25 mg | | |
|---|---|---|---|---|
| | | Batch No.: PB020049 | | |
| | | HDPE bottle (m) | PVC/PVDC (m) | Aluminium blister (m) |
| Dissolution | 25° C./60° C. | 0 months 95(min)–102 (max)/97(avg); 24 months 96–99/97 | 0 months 95(min)–102 (max)/97(avg); 24 months 96–99/97 | 0 months 95(min)–102 (max)/97(avg); 24 months 92–96/94 |
| | 30° C./70° C. | 0 months 95(min)–102 (max)/97(avg); 24 months 96–97/97 | 0 months 95(min)–102 (max)/97(avg); 24 months 96–98/97 | 0 months 95(min)–102 (max)/97(avg); 24 months 95–99/97 |
| | 40° C./75° C. | 0 months 95(min)–102 (max)/97(avg); 6 months 92–94/93 | 0 months 95(min)–102 (max)/97(avg); 6 months 91–94/93 | 0 months 95(min)–102 (max)/97(avg); 6 months 92–95/94 |
| Assay of Pimobendan | 25° C./60° C. | 0 months 1.251; 24 months 1.233 | 0 months 1.251; 24 months 1.236 | 0 months 1.251; 24 months 1.237 |
| | 30° C./70° C. | 0 months 1.251; 24 months 1.229 | 0 months 1.251; 24 months 1.242 | 0 months 1.251; 24 months 1.236 |
| | 40° C./75° C. | 0 months 1.251; 6 months 1.221 | 0 months 1.251; 6 months 1.214 | 0 months 1.251; 6 months 1.231 |
| Degradation of Pimobendan | 25° C./60° C. | 0 months 1)<0.10(K2006a); 2)<0.10(DU-CG 134 BS); 3)<0.10(any unspecified); 4)<0.10(total; 24 months 1)<0.10; 2)<0.10; 3)<0.10; 4)<0.10 | 0 months 1)<0.10(K2006a); 2)<0.10(DU-CG 134 BS); 3)<0.10(any unspecified); 4)<0.10(total); 24 months 1)<0.10; 2)<0.10; 3)<0.10; 4)<0.10 | 0 months 1)<0.10(K2006a); 2)<0.10(DU-CG 134 BS); 3)<0.10(any unspecified); 4)<0.10(total; 24 months 1)<0.10; 2)<0.10; 3)<0.10; 4)<0.10 |
| | 30° C./7° C. | 0 months 1)<0.10(K2006a); 2)<0.10(DU-CG 134 BS); 3)<0.10(any unspecified); 4)<0.10(total); 24 months 1)<0.10; 2)0.10; 3)<0.10; 4)0.10 | 0 months 1)<0.10(K2006a); 2)<0.10(DU-CG 134 BS); 3)<0.10(any unspecified); 4)<0.10(total); 24 months 1)0.35; 2)<0.10; 3)<0.10; 4)0.35 | 0 months 1)<0.10(K2006a); 2)<0.10(DU-CG 134 BS); 3)<0.10(any unspecified); 4)<0.10(total); 24 months 1)<0.10; 2)<0.10; 3)<0.10; 4)<0.10 |
| | 40° C./75° C. | 0 months 1)<0.10(K2006a); 2)<0.10(DU-CG 134 BS); 3)<0.10(any unspecified); 4)<0.10(total); 6 months 1)0.10; 2)0.11; 3)<0.10; 4)0.21 | 0 months 1)<0.10(K2006a); 2)<0.10(DU-CG 134 BS); 3)<0.10(any unspecified); 4)<0.10(total); 6 months 1)0.55; 2)<0.10; 3)<0.10; 4)0.55 | 0 months 1)<0.10(K2006a); 2)<0.10(DU-CG 134 BS); 3)<0.10(any unspecified); 4)<0.10(total); 6 months 1)<0.10; 2)<0.10; 3)<0.10; 4)<0.10 |
| | | Batch No.: PB020050 | | |
| | | HDPE bottle (m) | PVC/PVCD (m) | Aluminium blister (m) |
| Dissolution | 25° C./60° C. | 0 months 91(min)–96 (max)/94(avg); 24 months 96–104/99 | 0 months 91(min)–96 (max)/94(avg); 24 months 84–101/95 | 0 months 91(min)–96 (max)/94(avg); 24 months 92–96/94 |
| | 30° C./70° C. | 0 months 91(min)–96 (max)/94(avg); 24 months 94–102/97 | 0 months 91(min)–96 (max)/94(avg); 24 months 93–102/97 | 0 months 91(min)–96 (max)/94(avg); 24 months 97–105/99 |
| | 40° C./75° C. | 0 months 91(min)–96 (max)/94(avg); 6 months 91–92/91 | 0 months 91(min)–96 (max)/94(avg); 6 months 91–93/92 | 0 months 91(min)–96 (max)/94(avg); 6 months 91–92/91 |
| Assay of Pimobendan | 25° C./60° C. | 0 months 1.231; 24 months 1.224 | 0 months 1.231; 24 months 1.201 | 0 months 1.231; 24 months 1.228 |
| | 30° C./70° C. | 0 months 1.231; 24 months 1.213 | 0 months 1.231; 24 months 1.217 | 0 months 1.231; 24 months 1.230 |
| | 40° C./75° C. | 0 months 1.231; 6 months 1.205 | 0 months 1.231; 6 months 1.202 | 0 months 1.231; 6 months 1.215 |
| Degradation of Pimobendan | 25° C./60° C. | 0 months 1)<0.10(K2006a); 2)<0.10(DU-CG 134 BS); 3)<0.10(any unspecified); 4)<0.10(total); 24 months 1)<0.10; 2)<0.10; 3)<0.10; 4)<0.10 | 0 months 1)<0.10(K2006a); 2)<0.10(DU-CG 134 BS); 3)<0.10(any unspecified); 4)<0.10(total); 24 months 1)<0.10; 2)<0.10; 3)<0.10; 4)<0.10 | 0 months 1)<0.10(K2006a); 2)<0.10(DU-CG 134 BS); 3)<0.10(any unspecified); 4)<0.10(total); 24 months 1)<0.10; 2)<0.10; 3)<0.10; 4)<0.10 |

| | | Product: Pimobendan chewable tablets 1.25 mg | | |
|---|---|---|---|---|
| | 30° C./7° C. | 0 months 1)<0.10(K2006a); 2)<0.10(DU-CG 134 BS); 3)<0.10(any unspecified); 4)<0.10(total); 24 months1)<0.10; 2)<0.10; 3)<0.10; 4)<0.10 | 0 months 1)<0.10(K2006a); 2)<0.10(DU-CG 134 BS); 3)<0.10(any unspecified); 4)<0.10(total); 24 months 1)<0.37; 2)<0.10; 3)<0.10; 4)<0.37 | 0 months 1)<0.10(K2006a); 2)<0.10(DU-CG 134 BS); 3)<0.10(any unspecified); 4)<0.10(total); 24 months 1)<0.10; 2)<0.10; 3)<0.10; 4)<0.10 |
| | 40° C./75° C. | 0 months 1)<0.10(K2006a); 2)<0.10(DU-CG 134 BS); 3)<0.10(any unspecified); 4)<0.10(total); 6 months 1)<0.10; 2)<0.10; 3)<0.10; 4)<0.10 | 0 months 1)<0.10(K2006a); 2)<0.10(DU-CG 134 BS); 3)<0.10(any unspecified); 4)<0.10(total); 6 months 1)0.58; 2)<0.10; 3)<0.10; 4)0.58 | 0 months 1)<0.10(K2006a); 2)<0.10(DU-CG 134 BS); 3)<0.10(any unspecified); 4)<0.10(total); 6 months 1)<0.10; 2)<0.10; 3)<0.10; 4)<0.10 |

| | | Batch No.: PB020051 HDPE bottle (m) | PVC/PVDC (m) | Aluminium blister (m) |
|---|---|---|---|---|
| Dissolution | 25° C./60° C. | 0 months 92(min)–95(max)/94(avg); 24 months 92–100/96 | 0 months 92(min)–95(max)/94(avg); 24 months 94–101/97 | 0 months 92(min)–95(max)/94(avg); 24 months 91–100/95 |
| | 30° C./70° C. | 0 months 92(min)–95(max)/94(avg); 24 months 92–99/96 | 0 months 92(min)–95(max)/94(avg); 24 months 95–98/97 | 0 months 92(min)–95(max)/94(avg); 24 months 92–100/97 |
| | 40° C./75° C. | 0 months 92(min)–95(max)/94(avg); 6 months 91–93/92 | 0 months 92(min)–95(max)/94(avg); 6 months 90–92/91 | 0 months 92(min)–95(max)/94(avg); 6 months 91–94/92 |
| Assay of Pimobendan | 25° C./60° C. | 0 months 1.230; 24 months 1.222 | 0 months 1.230; 24 months 1.225 | 0 months 1.230; 24 months 1.228 |
| | 30° C./70° C. | 0 months 1.230; 24 months 1.214 | 0 months 1.230; 24 months 1.221 | 0 months 1.230; 24 months 1.230 |
| | 40° C./75° C. | 0 months 1.230; 6 months 1.210 | 0 months 1.230; 6 months 1.202 | 0 months 1.230; 6 months 1.218 |
| Degradation of Pimobendan | 25° C./60° C. | 0 months 1) <0.10(K2006a); 2)<0.10(DU-CG 134 BS); 3)<0.10(any unspecified); 4)<0.10(total); 24 months 1)<0.10; 2)<0.10; 3)<0.10; 4)<0.10 | 0 months 1)<0.10(K2006a); 2)<0.10(DU-CG 134 BS); 3)<0.10(any unspecified); 4)<0.10(total); 24 months 1)<0.10; 2)<0.10; 3)<0.10; 4)<0.10 | 0 months 1)<0.10(K2006a); 2)<0.10(DU-GG 134 BS); 3)<0.10(any unspecified); 4)<0.10(total); |
| | 30° C./7° C. | 0 months 1)<0.10(K2006a); 2)<0.10(DU-CG 134 BS); 3)<0.10(any unspecified); 4)<0.10(total); 24 months 1)<0.10; 2)<0.10; 3)<0.10; 4)<0.10 | 0 months 1)<0.10(K2006a); 2)<0.10(DU-CG 134 BS); 3)<0.10(any unspecified); 4)<0.10(total); 24 months 1)<0.33; 2)<0.10; 3)<0.10; 4)0.33 | 0 months 1)<0.10(K2006a); 2)<0.10(DU-CG 134 BS); 3)<0.10(any unspecified); 4)<0.10(total); |
| | 40° C./75° C. | 0 months 1)<0.10(K2006A); 2)<0.10(DU-CG 134 BS); 3)<0.10(any unspecified); 4)<0.10(total); 6 months 1)<0.10; 2)0.10; 3)<0.10; 4)0.10 | 0 months 1)<0.10(K2006a); 2)<0.10(DU-CG 134 BS); 3)<0.10(any unspecified); 4)<0.10(total); 6 months 1)<0.54; 2)<0.10; 3)<0.10; 4)0.54 | 0 months 1)<0.10(K2006a); 2)<0.10(DU-CG 134 BS); 3)<0.10(any unspecified); 4)<0.10(total); |

| | | Product: Pimobendan chewable tablets 2.5 mg | | |
|---|---|---|---|---|
| | | HDPE bottle (m) | PVC/PVDC (m) | Aluminium blister (m) |
| | | Batch No.: PB020052 | | |
| Dissolution | 30° C./70° C. | 0 months 97(min)–99(max)/98(avg); 12 Months 93–95/94 | 0 months 97(min)–99(max)/98(avg); 12 months 93–94/94 | 0 months 97(min)–99(max)/98(avg); 12 months 94–97/96 |
| | 40° C./75° C. | 0 months 97(min)–99(max)/98(avg); 6 months 93–94/93 | 0 months 97(min)–99(max)/98(avg); 6 months 91–93/92 | 0 months 97(min)–99(max)/98(avg); 6 months 93–95/94 |

| | | Product: Pimobendan chewable tablets 2.5 mg | | |
|---|---|---|---|---|
| | | HDPE bottle (m) | PVC/PVDC (m) | Aluminium blister (m) |
| Assay of Pimobendan | 30° C./70° C. | 0 months 2.49; 12 months 2.49 | 0 months 2.49; 12 months 2.47 | 0 months 2.49; 12 months 2.50 |
| | 40° C./75° C. | 0 months 2.49; 6 months 2.41 | 0 months 2.49; 6 months 2.41 | 0 months 2.49; 6 months 2.45 |
| Degradation of Pimobendan | 30° C./7° C. | 0 months 1)<0.10(K2006a); 2)<0.10(UDCG 134 BS); 3)<0.10 (any unspecified); 4)<0.10(total); 12 months 1)<0.10; 2)<0.10; 3)<0.10; 4)<0.10 | 0 months 1)<0.10(K2006a); 2)<0.10(UDCG 134 BS); 3)<0.10 (any unspecified); 4)<0.10(total); 12 months 1)<0.10; 2)<0.10; 3)<0.10; 4)<0.10 | 0 months 1)<0.10(K2006a); 2)<0.10(UDCG 134 BS); 3)<0.10 (any unspecified); 4)<0.10(total); 12 months 1)<0.10; 2)<0.10; 3)<0.10; 4)<0.10 |
| | 40° C./75° C. | 0 months 1)<0.10(K2006a); 2)<0.10(UDCG 134 BS); 3)<0.10 (any unspecified); 4)<0.10(total); 6 months 1)<0.10; 2)<0.10; 3)<0.10; 4)<0.10 | 0 months 1)<0.10(K2006a); 2)<0.10(UDCG 134 BS); 3)<0.10 (any unspecified); 4)<0.10(total); 6 months 1)0.43; 2)<0.10; 3)<0.10; 4)0.43 | 0 months 1)<0.10(K2006a); 2)<0.10(UDCG 134 BS); 3)<0.10 (any unspecified); 4)<0.10(total); 6 months 1)<0.10; 2)<0.10; 3)<0.10; 4)<0.10 |
| | | Batch No.: PB020053 | | |
| Dissolution | 30° C./70° C. | 0 months 96(min)–98 (max)/97(avg); 12 months 92–94/93 | 0 months 96(min)–98 (max)/97(avg); 12 months 90–93/92 | 0 months 96(min)–98 (max)/97(avg); 12 months 91–95/93 |
| | 40° C./75° C. | 0 months 96(min)–98 (max)/97(avg); 6 months 89–93/91 | 0 months 96(min)–98 (max)/97(avg); 6 months 91–91/91 | 0 months 96(min)–98 (max)/97(avg); 6 months 90–92/91 |
| Assay of Pimobendan | 30° C./70° C. | 0 months 2.44; 12 months 2.44 | 0 months 2.44; 12 months 2.41 | 0 months 2.44; 12 months 2.46 |
| | 40° C./75° C. | 0 months 2.44; 6 months 2.41 | 0 months 2.44; 6 months 2.40 | 0 months 2.44; 6 months 2.40 |
| Degradation of Pimobendan | 30° C./7° C. | 0 months 1)<0.10(K2006a); 2)<0.10(UDCG 134 BS); 3)<0.10 (any unspecified); 4)<0.10(total); 12 months 1)<0.10; 2)<0.10; 3)<0.10; 4)<0.10 | 0 months 1)<0.10(K2006a); 2)<0.10(UDCG 134 BS); 3)<0.10 (any unspecified); 4)<0.10(total); 12 months 1)<0.10; 2)<0.10; 3)<0.10; 4)<0.10 | 0 months 1)<0.10(K2006a); 2)<0.10(UDCG 134 BS); 3)<0.10 (any unspecified); 4)<0.10(total); 12 months 1)<0.10; 2)<0.10; 3)<0.10; 4)<0.10 |
| | 40° C./75° C. | 0 months 1)<0.10(K2006a); 2)<0.10(UDCG 134 BS); 3)<0.10 (any unspecified); 4)<0.10(total); 6 months 1)<0.10; 2)<0.10; 3)<0.10; 4)<0.10 | 0 months 1)<0.10(K2006a); 2)<0.10(UDCG 134 BS); 3)<0.10 (any unspecified); 4)<0.10(total); 6 months 1)0.39; 2)<0.10; 3)<0.10; 4)0.39 | 0 months 1)<0.10(K2006a); 2)<0.10(UDCG 134 BS); 3)<0.10 (any unspecified); 4)<0.10(total); 6 months 1)<0.10; 2)<0.10; 3)<0.10; 4)<0.10 |
| | | Batch No.: PB020054 | | |
| Dissolution | 30° C./70° C. | 0 months 96(min)–98 (max)/97(avg); 12 months 93–95/94 | 0 months 96(min)–98 (max)/97(avg); 12 months 90–93/91 | 0 months 96(min)–98 (max)/97(avg); 12 months 93–94/94 |
| | 40° C./75° C. | 0 months 96(min)–98 (max)/97(avg); 6 months 90–92/91 | 0 months 96(min)–98 (max)/97(avg); 6 months 90–92/91 | 0 months 96(min)–98 (max)/97(avg); 6 months 91–93/92 |
| Assay of Pimobendan | 30° C./70° C. | 0 months 2.45; 12 months 2.47 | 0 months 2.45; 12 months 2.45 | 0 months 2.45; 12 months 2.44 |
| | 40° C./75° C. | 0 months 2.45; 6 months 2.40 | 0 months; 6 months 2.39 | 0 months 2.45; 6 months 2.41 |
| Degradation of Pimobendan | 30° C./7° C. | 0 months 1)<0.10(K2006a); 2)<0.10(UDCG 134 BS); 3)<0.10 (any unspecified); 4)<0.10(total); 12 months 1)<0.10; 2)<0.10; 3)<0.10; 4)<0.10 | 0 months 1)<0.10(K2006a); 2)<0.10(UDCG 134 BS); 3)<0.10 (any unspecified); 4)<0.10(total); 12 months 1)<0.10; 2)<0.10; 3)<0.10; 4)<0.10 | 0 months 1)<0.10(K2006a); 2)<0.10(UDCG 134 BS); 3)<0.10 (any unspecified); 4)<0.10(total); 12 months 1)<0.10; 2)<0.10; 3)<0.10; 4)<0.10 |

-continued

| | | Product: Pimobendan chewable tablets 2.5 mg | | |
|---|---|---|---|---|
| | | HDPE bottle (m) | PVC/PVDC (m) | Aluminium blister (m) |
| | 40° C./75° C. | 0 months 1)<0.10(K2006a); 2)<0.10(UDCG 134 BS); 3)<0.10 (any unspecified); 4)<0.10(total); 6 months 1)<0.10; 2)<0.10; 3)<0.10; 4)<0.10 | 0 months 1)<0.10(K2006a); 2)<0.10(UDCG 134 BS); 3)<0.10 (any unspecified); 4)<0.10(total); 6 months 1)0.36; 2)<0.10; 3)<0.10; 4)0.36 | 0 months 1)<0.10(K2006a); 2)<0.10(UDCG 134 BS); 3)<0.10 (any unspecified); 4)<0.10(total); 6 months 1)<0.10; 2)<0.10; 3)<0.10; 4)<0.10 |

| | | Product: Pimobendan chewable tablets 5 mg | | |
|---|---|---|---|---|
| | | HDPE bottle (m) | PVC/PVDC (m) | Aluminium blister (m) |
| | | Batch No.: PB020059 | | |
| Dissolution | 25° C./60% | 0 months 94 (min)–96 (max)/95 (avg); 24 months 83–90/88 | 0 months 94 (min)–96 (max)/95 (avg); 24 months 83–92/88 | 0 months 94 (min)–96 (max)/95 (avg); 24 months 85–89/87 |
| | 30° C./70° C. | 0 months 94 (min)–96 (max)/95 (avg); 24 months 83–95/89 | 0 months 94 (min)–96 (max)/95 (avg); 24 months 82–97/88 | 0 months 94 (min)–96 (max)/95 (avg); 24 months 83–91/87 |
| | 40° C./75° C. | 0 months 94 (min)–96 (max)/95 (avg); 6 months 91–92/91 | 0 months 94 (min)–96 (max)/95 (avg); 6 months 90–92/91 | 0 months 94 (min)–96 (max)/95 (avg); 6 months 81–93/92 |
| Assay of Pimobendan | 25° C./60% | 0 month 4.95; 24 month 4.94 | 0 month 4.95; 24 month 4.92 | 0 month 4.95; 24 month 4.92 |
| | 30° C./70° C. | 0 month 4.95; 24 month 4.90 | 0 month 4.95; 24 month 4.92 | 0 month 4.95; 24 month 4.96 |
| | 40° C./75° C. | 0 month 4.95; 6 month 4.88 | 0 month 4.95; 6 month 4.91 | 0 month 4.95; 6 month 4.95 |
| Degradation of Pimobendan | 25° C./60% | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10 | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10 | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10 |
| | 30° C./7° C. | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10 | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10 | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10 |
| | 40° C./75° C. | 0 months 1)<0.10 (K2006a); 2) <0.10 (UD-CG 134 BS); 3) <0.10 (any unspecified); 4) <0.10 (total); 6 months 1) <0.10; 2) <0.10; 3) <0.10; 4) <0.10 | 0 months 1)<0.10 (K2006a); 2) <0.10 (UD-CG 134 BS); 3) <0.10 (any unspecified); 4) <0.10 (total); 6 months 1) 0.23; 2) <0.10; 3) <0.10; 4) 0.23 | 0 months 1)<0.10 (K2006a); 2) <0.10 (UD-CG 134 BS); 3) <0.10 (any unspecified); 4) <0.10 (total); 6 months 1) <0.10; 2) <0.10; 3) <0.10; 4) <0.10 |
| | | Batch No.: PB020060 | | |
| Dissolution | 25° C./60% | 0 months 91 (min)–94 (max)/92 (avg); 24 months 85–90/87 | 0 months 91 (min)–94 (max)/92 (avg); 24 months 84–90/86 | 0 months 91 (min)–94 (max)/92 (avg); 24 months 82–88/86 |
| | 30° C./70° C. | 0 months 91 (min)–94 (max)/92 (avg); 24 months 85–90/87 | 0 months 91 (min)–94 (max)/92 (avg); 24 months 82–90/87 | 0 months 91 (min)–94 (max)/92 (avg); 24 months 86–90/88 |
| | 40° C./75° C. | 0 months 94 (min)–96 (max)/95 (avg); 6 months 88–89/89 | 0 months 91 (min)–94 (max)/92 (avg); 6 months 88–90/89 | 0 months 91 (min)–94 (max)/92 (avg); 6 months 89–92/90 |

-continued

| | | Product: Pimobendan chewable tablets 5 mg | | |
|---|---|---|---|---|
| | | HDPE bottle (m) | PVC/PVDC (m) | Aluminium blister (m) |
| Assay of Pimobendan | 25° C./60% | 0 month 4.87; 24 month 4.88 | 0 month 4.87; 24 month 4.86 | 0 month 4.87; 24 month 4.90 |
| | 30° C./70° C. | 0 month 4.87; 24 month 4.83 | 0 month 4.87; 24 month 4.86 | 0 month 4.84; 24 month 4.89 |
| | 40° C./75° C. | 0 month 4.87; 6 month 4.86 | 0 month 4.87; 6 month 4.87 | 0 month 4.87; 6 month 4.86 |
| Degradation of Pimobendan | 25° C./60% | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; |
| | 30° C./7° C. | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; |
| | 40° C./75° C. | 0 months 1)<0.10 (K2006a); 2) <0.10 (UD-CG 134 BS); 3) <0.10 (any unspecified); 4) <0.10 (total); 6 months 1) <0.10; 2) <0.10; 3) <0.10; 4) <0.10 Batch No.: PB020061 | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; 6 months 1) 0.22; 2) <0.10; 3) <0.10; 4) 0.22 | 0 months 1)<0.10 (K2006a); 2) <0.10 (UD-CG 134 BS); 3) <0.10 (any unspecified); 4) <0.10 (total); 6 months 1) <0.10; 2) <0.10; 3) <0.10; 4) <0.10 |
| Dissolution | 25° C./60% | 0 months 92 (min)–95 (max)/94 (avg); 24 months 83–90/87 | 0 months 92 (min)–95 (max)/94 (avg); 24 months 86–91/88 | 0 months 92 (min)–95 (max)/94 (avg); 24 months 65–92/84 |
| | 30° C./70° C. | 0 months 92 (min)–95 (max)/94 (avg); 24 months 84–88/87 | 0 months 92 (min)–95 (max)/94 (avg); 24 months 81–87/85 | 0 months 92 (min)–95 (max)/94 (avg); 24 months 88–91/90 |
| | 40° C./75° C. | 0 months 92 (min)–95 (max)/94 (avg); 6 months 88–90/89 | 0 months 92 (min)–95 (max)/94 (avg); 6 months 88–90/89 | 0 months 92 (min)–95 (max)/94 (avg); 6 months 88–91/90 |
| Assay of Pimobendan | 25° C./60% | 0 month 4.87; 24 month 4.83 | 0 month 4.87; 24 month 4.85 | 0 month 4.87; 24 month 4.88 |
| | 30° C./70° C. | 0 month 4.87; 24 month 4.82 | 0 month 4.87; 24 month 4.80 | 0 month 4.87; 24 month 4.90 |
| | 40° C./75° C. | 0 month 4.87; 6 month 4.83 | 0 month 4.87; 6 month 4.82 | 0 month 4.87; 6 month 4.88 |
| Degradation of Pimobendan | 25° C./60% | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10 |
| | 30° C./7° C. | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; | 0 months 1)<0.10 (K2006a); 2) <0.10 (UD-CG 134 BS); 3) <0.10 (any unspecified); 4) <0.10 (total); 24 months 1) <0.10; 2) <0.10; 3) <0.10; 4) <0.10; |

| Product: Pimobendan chewable tablets 5 mg | | | |
|---|---|---|---|
| | HDPE bottle (m) | PVC/PVDC (m) | Aluminium blister (m) |
| 40° C./75° C. | 0 months 1)<0.10 (K2006a); 2) <0.10 (UD-CG 134 BS); 3) <0.10 (any unspecified); 4) <0.10 (total); 6 months 1) <0.10; 2) <0.10; 3) <0.10; 4) <0.10 | 0 months 1)<0.10 (K2006a); 2) <0.10 (UD-CG 134 BS); 3) <0.10 (any unspecified); 4) <0.10 (total); 6 months 1) 0.22; 2) <0.10; 3) <0.10; 4) 0.22 | 0 months 1)<0.10 (K2006a); 2) <0.10 (UD-CG 134 BS); 3) <0.10 (any unspecified); 4) <0.10 (total); 6 months 1) <0.10; 2) <0.10; 3) <0.10; 4) <0.10 |

What is claimed is:

1. A solid formulation comprising a homogenous dispersion of:
   pimobendan or a pharmaceutically acceptable salt thereof provided in an amount of 0.5 mg to 20 mg;
   a polyvalent acid selected from the group consisting of citric acid, tartaric acid, an anhydride thereof and mixtures thereof, wherein the polyvalent acid is present in an amount of 2.5 percent to 10 percent by weight of said solid formulation, and wherein the solid formulation includes a weight ratio of 1:10 to 1:40 of pimobendan to polyvalent acid; and
   a flavor acceptable to small animals, wherein the flavor is present in an amount of 5 to 30 percent by weight of said solid formulation.

2. The solid formulation of claim 1, further comprising carriers or excipients, where the carriers or excipients are selected from the group consisting of diluents, disintegrants, carriers, binders, flow regulators, lubricants, solvents and mixtures thereof.

3. The solid formulation of claim 2, further comprising starch and lactose.

4. The solid formulation of claim 3, wherein the starch is selected from the group consisting of native starch, gelatinized starch, partly gelatinized starch, starch powder, starch granules, chemically modified starch, swellable physically modified starch and mixtures thereof.

5. The solid formulation of claim 4, wherein the starch is corn starch.

6. The solid formulation of claim 3, wherein the lactose consists of coarse particles greater than 200 μm in size.

7. The solid formulation of claim 1, comprising 1.25 mg, 2.5 mg, 5 mg, or 10 mg of pimobendan.

8. The solid formulation of claim 1, wherein the weight of the whole solid formulation is in the range of 250 to 3000 mg.

9. The solid formulation of claim 1, wherein the solid formulation is a tablet or a granule.

10. The solid formulation of claim 1, wherein the solid formulation comprises 1.25 mg, 2.5 mg, 5 mg or 10 mg pimobendan, and lactose, corn starch, croscarmellose-sodium, 50 mg/g citric acid, artificial beef flavor, polyvidone, colloidal anhydrous silica and magnesium stearate.

11. A solid formulation comprising a homogenous dispersion of:
   pimobendan or a pharmaceutically acceptable salt thereof provided in an amount of 0.5 mg to 20 mg;
   a polyvalent acid selected from the group consisting of citric acid, tartaric acid, an anhydride thereof and mixtures thereof, wherein the polyvalent acid is present in an amount of 2.5 percent to 10 percent by weight of said solid formulation, and wherein the solid formulation includes a weight ratio of 1:10 to 1:40 of pimobendan to polyvalent acid;
   starch in an amount of 25 to 50 percent by weight of said solid formulation;
   lactose in an amount of 25 to 50 percent by weight of said solid formulation; and
   a flavor acceptable to small animals, wherein the flavor is present in an amount of 5 to 30 percent by weight of said solid formulation.

12. The solid formulation of claim 11, comprising 1.25 mg, 2.5 mg, 5 mg or 10 mg of pimobendan.

13. The solid formulation of claim 11, characterized in that the solid formulation is a tablet or a granule.

14. The solid formulation of claim 1, wherein the solid formulation exhibits a dissolution profile, utilizing a paddle dissolution method at a rotation speed 75 RPM and a buffer pH of 4.0, in which a majority of the solid formulation has dissolved at 30 minutes.

15. The solid formulation of claim 11, wherein the solid formulation exhibits a dissolution profile, utilizing a paddle dissolution method at a rotation speed 75 RPM and a buffer pH of 4.0, in which a majority of the solid formulation has dissolved at 30 minutes.

16. The solid formulation of claim 1, wherein the content uniformity of the pimobendan or the pharmaceutically acceptable salt thereof is 94.8 percent or greater.

17. The solid formulation of claim 11, wherein the content uniformity of the pimobendan or the pharmaceutically acceptable salt thereof is 94.8 percent or greater.

18. The solid formulation of claim 1, wherein the flavor is homogenously dispersed within the solid formulation.

19. The solid formulation of claim 1, wherein the solid formulation is obtained by an aqueous manufacturing process.

20. The solid formulation of claim 1, wherein the solid formulation is obtained by an aqueous fluid-bed granulation process.

21. The solid formulation of claim 1, wherein the solid formulation is obtained by a fluid-bed granulation process, the fluid-bed granulation process comprising the following steps:
   a) spraying an aqueous solution of pimobendan and a binder onto a solid support comprising at least one excipient, a flavor and citric acid anhydrous to form a mixture;
   b) drying the mixture of a);
   c) sieving and de-agglomerating the mixture of b);
   d) adding a flow regulator to the mixture of c);
   e) adding a lubricant to the mixture of d); and
   f) blending the mixture of e) for uniformity of granules to obtain final granules.

22. The solid formulation of claim 21, wherein the fluid-bed granulation process further comprises:

g) compressing the final granules of f) to tablets.

23. The solid formulation of claim 16, wherein the content uniformity is blend uniformity.

24. The solid formulation of claim 16, wherein the content uniformity of the pimobendan or the pharmaceutically acceptable salt thereof is at least 98.0 percent.

* * * * *